United States Patent
Connolly et al.

(10) Patent No.: US 7,276,528 B2
(45) Date of Patent: Oct. 2, 2007

(54) COMPOUNDS FOR THE INHIBITION OF NITRIC OXIDE SYNTHASE

(75) Inventors: Stephen Connolly, Loughborough (GB); Glen Ernst, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/440,994

(22) Filed: May 25, 2006

(65) Prior Publication Data

US 2006/0217424 A1    Sep. 28, 2006

Related U.S. Application Data

(62) Division of application No. 10/491,264, filed as application No. PCT/SE02/01803 on Oct. 2, 2002, now Pat. No. 7,119,122.

(30) Foreign Application Priority Data

Oct. 4, 2001  (SE) ................................ 0103325

(51) Int. Cl.
  *A61K 31/4412*  (2006.01)
  *C07D 213/85*  (2006.01)
(52) U.S. Cl. ...................... 514/344; 546/288
(58) Field of Classification Search ............ None
See application file for complete search history.

(56) References Cited

FOREIGN PATENT DOCUMENTS

| EP | 0 262 870 A2 | 4/1988 |
|---|---|---|
| GB | 1264340 A1 | 2/1972 |
| WO | WO94/02448 A1 | 2/1994 |
| WO | WO97/17325 A1 | 5/1997 |
| WO | WO 00/23420 | 4/2000 |
| WO | WO 01/36413 A1 | 5/2001 |
| WO | WO 02/06276 A2 | 1/2002 |

OTHER PUBLICATIONS

Alderton et al. Biochem. J. 2001, 357, 593-615.*
Kubes et al. The American Journal of Medicine Aug. 1, 2000.*
Thomsen et al. Annals New York Academy of Sciences 1997, 835, 363-372.*
Kmonicek et al., STN International, File HCAPLUS, No. 1992:105741, Doc. 116:105741.
Vercouillie et al., Journal of Labelled Compounds and Radiopharmaceuticals, 2001, vol. 44, 113-120.
Glinka, STN International, File CAPLUS, No. 1984: 191848, Doc. 100:161848.
Ol, et al. STN International, File CAPLUS, No. 2000:277959, Doc. 132:321662.
Oya et al., Nuclear Medicine & Biology, 2000, vol. 27, 249-254.
Tarkiainen et al., Journal of Labelled Compounds and Radiopharmaceuticals, 2001, vol. 44, 113-120.
Emond et al., J. Med. Chem., 2002, vol. 45, 1253-1258.

* cited by examiner

*Primary Examiner*—Rebecca Anderson
*Assistant Examiner*—Jason M Nolan
(74) *Attorney, Agent, or Firm*—White & Case LLP

(57) ABSTRACT

There are provided novel compounds of formula (I)

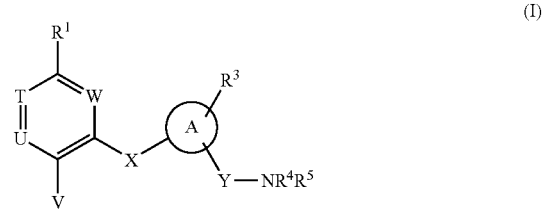

wherein A, $R^1$, $R^3$, $R^4$, $R^5$, T, U, V, W, X and Y are as defined in the specification, and pharmaceutically acceptable salts thereof; together with processes for their preparation, compositions containing them and their use in therapy. The compounds are inhibitors of nitric oxide synthase and are thereby particularly useful in the treatment or prophylaxis of inflammatory diseases, pain and CNS diseases.

12 Claims, No Drawings

COMPOUNDS FOR THE INHIBITION OF NITRIC OXIDE SYNTHASE

This application is a divisional of U.S. application Ser. No. 10/491,264 now U.S. Pat. No. 7,119,122, filed Mar. 30, 2004, which is the National Stage of International Application No. PCT/SE02/01803, filed Oct. 2, 2002, which claims benefit of Swedish Application No. 0103325-7, filed Oct. 4, 2001.

FIELD OF THE INVENTION

The present invention relates to novel phenylalkylamine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (eNOS) is involved with smooth muscle relaxation and the regulation of blood pressure and blood flow, whereas the neuronal enzyme (nNOS) appears to be involved in the regulation of various biological functions. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221-230).

Considerable effort has been expended in efforts to identify compounds that act as specific inhibitors of one or more isoforms of the enzyme nitric oxide synthase. The use of such compounds in therapy has also been widely claimed. 2-(2-Nitrophenoxy)benzenemethanamine,

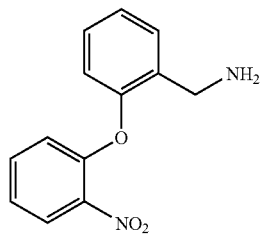

is disclosed in *Polish J Chem.*, 1982, 56, 1139-1144 as an intermediate in the synthesis of N,N'-disubstituted derivatives of dibenzo-[b.h]-tetrahydro-1,4,6-oxadiazonine.

WO 94/12163 discloses 2-nitroaryl compounds of general formula

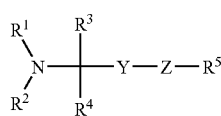

that are regulators of nitric oxide synthase.

WO 97/17325 discloses compounds of general formula

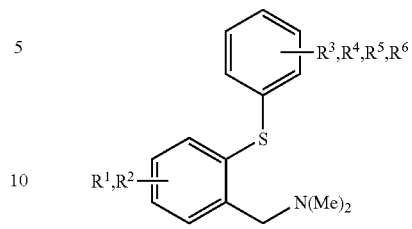

These compounds are serotonin re-uptake inhibitors useful in the treatment of depression.

DISCLOSURE OF THE INVENTION

According to the present invention, there is provided a compound of formula (I)

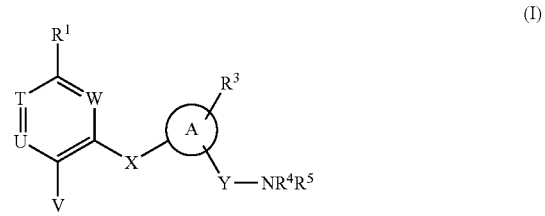

(I)

wherein:

A represents a phenyl ring or A represents a C8 to 10 aromatic or partially aromatic bicyclic ring system;

$R^1$ represents C1 to 6 alkyl, C1 to 6 alkoxy, halogen, hydroxy, cyano, trifluoromethyl or $NR^6R^7$;

$R^3$ represents hydrogen, C1 to 6 alkyl, C2 to 6 alkenyl, C3 to 6 cycloalkyl, C1 to 6 alkylthio, C1 to 6 alkoxy, halogen, hydroxy, cyano, trifluoromethyl or $NR^8R^9$; said alkoxy group being optionally further substituted by hydroxy or by one or more fluorine atoms.

or $R^3$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, hydroxy, cyano or $NR^8R^9$; said alkyl or alkoxy group being optionally further substituted by one or more fluorine atoms;

$R^4$ and $R^5$ independently represent hydrogen or C1 to 6 alkyl; said alkyl group being optionally substituted by OH, C1 to 6 alkoxy, $NR^{10}R^{11}$ or phenyl; said phenyl group being optionally further substituted by C1 to 6 alkyl, C1 to 6 alkoxy, halogen, hydroxy, cyano or $NR^{12}R^{13}$;

$R^6$, $R^7$, $R^8$, $R^9$, $R^{10}$, $R^{11}$, $R^{12}$ and $R^{13}$ independently represent hydrogen or C1 to 6 alkyl;

said alkyl group being optionally substituted by OH or C1 to 6 alkoxy;

or the groups $NR^4R^5$, $NR^6R^7$ and $NR^8R^9$ independently represent a 4 to 7 membered saturated azacyclic ring optionally incorporating one further heteroatom selected from O or N; said ring being optionally substituted by OH, C1 to 3 hydroxyalkyl or C1 to 3 alkoxy;

V represents cyano or nitro;

X represents O or $S(O)_n$;

n represents an integer 0, 1 or 2;

Y represents C1 to 6 alkyl;

Either one of T, U and W represents N and the other two independently represent $CR^2$; or each of T, U and W represents $CR^2$; and each $R^2$ group independently represents hydrogen, C1 to 3 alkyl, C1 to 3 alkoxy or halogen;

or a pharmaceutically acceptable salt thereof;

with the proviso that when A represents phenyl, V represents nitro, Y represents $CH_2$, X represents S, each of T, U and W represents $CR^2$ and the group $Y—NR^4R^5$ is bonded to the phenyl ring ortho to X, then $R^4$ and $R^5$ do not both represent $CH_3$.

The compounds of formula I may exist in enantiomeric forms. Therefore, all enantiomers, diastereomers, racemates and mixtures thereof are included within the scope of the invention.

The compounds of formula (I) and their pharmaceutically acceptable salts have the advantage that they are inhibitors of the enzyme nitric oxide synthase (NOS). In general, the compounds of formula (I) and their pharmaceutically acceptable salts have the advantage that they are inhibitors of the inducible isoform of the enzyme nitric oxide synthase (iNOS). Certain compounds of formula (I) and their pharmaceutically acceptable salts have the advantage that they are additionally or alternatively inhibitors of the neuronal isoform of the enzyme nitric oxide synthase (nNOS). In general, compounds of formula (I) and their pharmaceutically acceptable salts have the advantage that they show good selectivity for the inhibition of iNOS and/or nNOS in comparison to the inhibition of the endothelial isoform, eNOS.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of nitric oxide synthase activity is beneficial.

Another aspect of the invention provides the use of a compound of formula (I) or a pharmaceutically acceptable salt thereof, in the manufacture of a medicament, for the treatment or prophylaxis of diseases or conditions in which inhibition of iNOS activity is beneficial.

Another aspect of the invention provides the use of a compound of formula (I) or a pharmaceutically acceptable salt thereof, in the manufacture of a medicament, for the treatment or prophylaxis of diseases or conditions in which inhibition of nNOS activity is beneficial.

Another aspect of the invention provides the use of a compound of formula (I) or a pharmaceutically acceptable salt thereof, in the manufacture of a medicament, for the treatment or prophylaxis of inflammatory disease.

Another aspect of the invention provides the use of a compound of formula (I) or a pharmaceutically acceptable salt thereof, in the manufacture of a medicament, for the treatment or prophylaxis of CNS disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt thereof.

There is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

There is also provided a method of treating, or reducing the risk of, CNS disease in a person suffering from or at risk of, said disease, wherein the method comprises administering to the person a therapeutically effective amount of a compound of formula (I) or a pharmaceutically acceptable salt thereof.

The compounds of the present invention may also be used advantageously in combination with a second pharmaceutically active substance; particularly in combination with a cyclooxygenase inhibitor; more particularly in combination with a selective inhibitor of the inducible isoform of cyclooxygenase (COX-2). Thus, in a further aspect of the invention there is provided the use of a compound of formula (I) or a pharmaceutically acceptable salt thereof, in combination with a COX-2 inhibitor in the manufacture of a medicament for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt thereof in combination with a COX-2 inhibitor.

In one embodiment, X in formula (I) represents oxygen.

In another embodiment, X in formula (I) represents $S(O)_n$ and n represents 0.

In one embodiment, V in formula (I) represents cyano.

In one embodiment, A in formula (I) represents phenyl.

In one embodiment, $R^3$ in formula (I) represents hydrogen, C1 to 6 alkoxy, hydroxy, or optionally substituted phenyl.

In one embodiment, $R^4$ and $R^5$ in formula (I) independently represent hydrogen or methyl.

In one embodiment, Y in formula (I) represents $CH_2$.

In one embodiment, T, U and W in formula (I) each independently represent CH or CF.

In another embodiment, T represents N and U and W each independently represent CH or CF.

In another embodiment, W represents N and T and U each independently represent CH or CF.

In one embodiment, A represents phenyl, $R^1$ represents C1 to 6 alkyl, C1 to 6 alkoxy, halogen, hydroxy, cyano, trifluoromethyl or $NR^6R^7$; X represents oxygen or $S(O)_n$ and n represents 0; V represents cyano; $R^3$ represents hydrogen, C1 to 6 alkoxy, hydroxy, or optionally substituted phenyl; $R^4$ and $R^5$ independently represent hydrogen or methyl; Y represents $CH_2$; and T, U and W in formula (I) each independently represent CH or CF; or T represents N and U and W each independently represent CH or CF; or W represents N and T and U each independently represent CH or CF.

In one embodiment, A represents a phenyl ring; $R^3$ represents hydrogen, C1 to 6 alkyl, C3 to 6 cycloalkyl, C1 to 6 alkylthio, C1 to 6 alkoxy, halogen, hydroxy, cyano, trifluoromethyl or $NR^8R^9$; or $R^3$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, hydroxy, cyano or $NR^8R^9$; said alkyl or alkoxy group being optionally further substituted by one or more fluorine atoms; $R^4$ and $R^5$ independently represent hydrogen or C1 to 6 alkyl; said alkyl group being optionally substituted by OH, C1 to 6 alkoxy or phenyl; said phenyl group being optionally further substituted by C1 to 6 alkyl, C1 to 6 alkoxy, halogen, hydroxy, cyano or $NR^{12}R^{13}$; and all other groups are as defined in formula (I) above.

Particular compounds of the invention include:
3-(5-methoxy-2-nitrophenoxy)benzenemethanamine;
3-(5-methyl-2-nitrophenoxy)benzenemethanamine;
3-(5-chloro-2-nitrophenoxy)benzenemethanamine;
3-(5-fluoro-2-nitrophenoxy)benzenemethanamine;
3-(5-methylamino-2-nitrophenoxy)benzenemethanamine;
3-(5-methyl-2-nitrophenylthio)benzenemethanamine;
2-[3-(aminomethyl)phenoxy]-4-chlorobenzonitrile;
4-chloro-2-[3-hydroxy-5-[(methylamino)methyl]phenoxy]benzonitrile;
4-chloro-2-[3-methoxy-5-[(methylamino)methyl]phenoxy]benzonitrile;
4-chloro-2-(3-methylaminomethyl-phenoxy)-benzonitrile;
4-chloro-2-(4-methoxy-3-methylaminomethyl-phenoxy)-benzonitrile;
4-chloro-2-(2-methoxy-3-methylaminomethyl-phenoxy)-benzonitrile;
4-chloro-2-(2-methoxy-4-methylaminomethyl-phenoxy)-benzonitrile;
4-chloro-2-(3-methoxy-4-methylaminomethyl-phenoxy)-benzonitrile;
2-(4-bromo-3-methylaminomethyl-phenoxy)-4-trifluoromethyl-benzonitrile;
2-(2-methylaminomethyl-biphenyl-4-yloxy)-4-trifluoromethyl-benzonitrile;
4-chloro-2-[2-hydroxy-3-(methylaminomethyl)phenoxy]benzonitrile;
4-chloro-2-[2-ethoxy-3-(methylaminomethyl)phenoxy]benzonitrile;
4-chloro-2-[2-(2-fluoroethoxy)-3-(methylaminomethyl)phenoxy]benzonitrile;
4-chloro-2-[3-methylaminomethyl-2-(2,2,2-trifluoroethoxy)phenoxy]-benzonitrile;
4-chloro-2-(3-methylaminomethyl-2-propoxyphenoxy)benzonitrile;
4-chloro-2-[2-(2-hydroxyethoxy)-3-(methylaminomethyl)phenoxy]-benzonitrile;
4-chloro-2-[2-ethoxy-4-(methylaminomethyl)phenoxy]benzonitrile;
4-chloro-2-[4-(methylaminomethyl)naphthalen-1-yloxy]benzonitrile;
4-chloro-2-[3-(dimethylaminomethyl)phenoxy]benzonitrile;
4-chloro-2-{3-[(2-(hydroxyethyl)amino)methyl]phenoxy}benzonitrile;
4-chloro-2-{3-[(2-methoxyethylamino)methyl]phenoxy}benzonitrile;
4-chloro-2-[3-(propylaminomethyl)phenoxy]benzonitrile;
4-chloro-2-{3-[(2-dimethylaminoethylamino)methyl]phenoxy}benzonitrile;
4-chloro-2-{3-[(3-hydroxypropylamino)methyl]phenoxy}benzonitrile;
4-chloro-2-[3-(pyrrolidin-1-ylmethyl)phenoxy]benzonitrile;
4-chloro-5-fluoro-2-(2-methoxy-3-methylaminomethylphenoxy)benzonitrile;
4-bromo-2-(2-methoxy-3-methylaminomethyl-phenoxy)-benzonitrile;
2-(2-methoxy-3-methylaminomethyl-phenoxy)-6-trifluoromethyl-nicotinonitrile;
4-methoxy-2-(2-methoxy-3-methylaminomethyl-phenoxy)-benzonitrile;
3-fluoro-2-(2-methoxy-3-(methylaminomethyl)phenoxy)-4-methyl-benzonitrile;
2-(2-methoxy-3-methylaminomethyl-phenoxy)-6-methyl-nicotinonitrile;
6-ethyl-2-(2-methoxy-3-methylaminomethyl-phenoxy)-nicotinonitrile;
4-methyl-2-(3-methylaminomethyl-phenoxy)-benzonitrile;
6-methyl-2-(3-methylaminomethyl-phenoxy)-nicotinonitrile;
4-chloro-2-(5-methylamino-5,6,7,8-tetrahydronaphthalen-1-yloxy)-benzonitrile;
4-chloro-2-(1-methylaminoindan-4-yloxy)benzonitrile;
[2-methoxy-3-(5-methyl-2-nitrophenoxy)benzyl]methylamine;
4-chloro-2-(3-dimethylaminomethyl-2-ethylphenoxy)benzonitrile;
2-(3-aminomethyl-2-ethyl-phenoxy)-4-chloro-benzonitrile;
4-chloro-2-(2-ethyl-3-methylaminomethyl-phenoxy)-benzonitrile;
4-chloro-2-(3-dimethylaminomethyl-2-propylphenoxy)-benzonitrile;
2-(3-aminomethyl-2-propyl-phenoxy)-4-chloro-benzonitrile;
4-chloro-2-(3-methylaminomethyl-2-propyl-phenoxy)-benzonitrile;
2-(2-allyl-4-methylaminomethyl-phenoxy)-4-chlorobenzonitrile;
4-chloro-2-(3-dimethylaminomethyl-4-fluorophenoxy)benzonitrile;
4-chloro-2-(4-fluoro-3-methylaminomethyl-phenoxy)-benzonitrile;
2-(2-methoxy-3-methylaminomethyl-phenoxy)-4-trifluoromethyl-benzonitrile;
2-(4-methylaminomethyl-3-phenyl-phenoxy)-4-trifluoromethyl-benzonitrile;
4-chloro-2-(3-dimethylaminomethyl-2-methysulfanyl-phenoxy)-benzonitrile;
4-chloro-2-(3-aminomethyl-2-methysulfanyl-phenoxy)-benzonitrile;
4-chloro-2-(2-methylsulfanyl-3-methylaminomethyl-phenoxy)-benzonitrile;
4-chloro-2-(3-dimethylaminomethyl-2-ethylsulfanyl-phenoxy)-benzonitrile;
4-chloro-2-(3-aminomethyl-2-ethylsulfanyl-phenoxy)-benzonitrile;
4-chloro-2-(2-ethysulfanyl-3-methylaminomethyl-phenoxy)-benzonitrile;

and pharmaceutically acceptable salts thereof.

Unless otherwise indicated, the term "C1 to 6 alkyl" referred to herein denotes a straight or branched chain alkyl group having from 1 to 6 carbon atoms. Examples of such groups include methyl, ethyl, n-propyl, i-propyl, n-butyl, i-butyl and t-butyl.

The terms "C1 to 3 alkyl" and "C1 to 4 alkyl" are to be interpreted analogously.

Unless otherwise indicated, the term "C1 to 6 alkoxy" referred to herein denotes a straight or branched chain alkoxy group having from 1 to 6 carbon atoms. Examples of such groups include methoxy, ethoxy, n-propoxy, i-propoxy and t-butoxy.

The terms "C1 to 3 alkoxy", "C1 to 4 alkoxy" and "C1 to 6 alkylthio" are to be interpreted analogously.

Unless otherwise indicated, the term "C1 to 3 hydroxyalkyl" referred to herein denotes a straight or branched chain alkyl group having from 1 to 3 carbon atoms substituted by OH. Examples of such groups include hydroxymethyl, 1-hydroxyethyl, 2-hydroxyethyl and 2-hydroxy-2-methylethyl.

Unless otherwise indicated, the term "C2 to 6 alkenyl" referred to herein denotes a straight or branched chain alkyl group having from 2 to 6 carbon atoms and including a carbon-carbon double bond. Examples of such groups include ethenyl, 1-propenyl, 2-propenyl and butenyl.

Unless otherwise indicated, the term "C3 to 6 cycloalkyl" referred to herein denotes a carbocyclic ring having from 3 to 6 carbon atoms. Examples of such groups include cyclopropyl, cyclopentyl and cyclohexyl.

Halogen represents fluoro, chloro, bromo or iodo.

Examples of a C8 to 10 aromatic or partially aromatic bicyclic ring system include indanyl, naphthyl and tetrahydronaphthyl.

Examples of a five or six membered aromatic heterocyclic ring containing 1 to 3 heteroatoms independently selected from O, S and N include furan, thiophene, pyrrole, thiazole, oxazole, imidazole, pyridine, pyrimidine and pyrazine.

Examples of a 4 to 7 membered saturated azacyclic ring optionally incorporating one further heteroatom selected from O or N include pyrrolidine, piperidine, piperazine, morpholine and perhydroazepine.

According to the invention, we further provide a process for the preparation of compounds of formula (I), or a pharmaceutically acceptable salt, enantiomer or racemate thereof which comprises:

(a) reaction of a compound of formula (II)

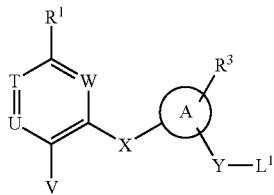
(II)

wherein A, $R^1$, $R^3$, T, U, V, W, X and Y are as defined in formula (I) and $L^1$ is a leaving group, with a compound of formula (III)

(III)

wherein $R^4$ and $R^5$ are as defined in formula (I); or (b) reductive amination of a compound of formula (IV)

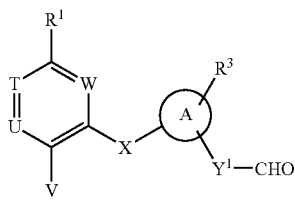
(IV)

wherein A, $R^1$, $R^3$, T, U, V, W and X are as defined in formula (I) and $Y^1$—$CH_2$ represents Y as defined in formula (I), with a compound of formula (III)

(III)

wherein $R^4$ and $R^5$ are as defined in formula (I); or (c) reaction of a compound of formula (V)

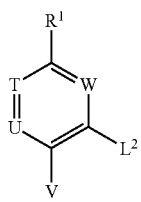
(V)

wherein $R^1$, T, U, V and W are as defined in formula (I) and $L^2$ is a leaving group, with a compound of formula (VI)

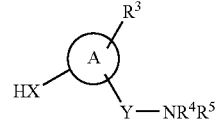
(VI)

wherein A, $R^3$, $R^4$, $R^5$ and Y are as defined in formula (I) and X is O or S; or (d) reaction of a compound of formula (VII)

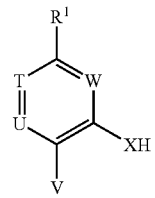
(VII)

wherein $R^1$, T, U, V and W are as defined in formula (I) and X represents O or S, with a compound of formula (VIII)

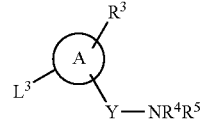
(VIII)

wherein A, $R^3$, $R^4$, $R^5$ and Y are as defined in formula (I) and $L^3$ is a leaving group; or (e) preparing a compound of formula (I) wherein $R^4$ and $R^5$ each represent hydrogen, by reduction of a compound of formula (IX)

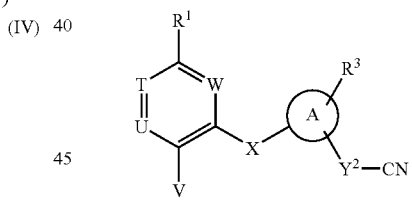
(IX)

wherein A, $R^1$, $R^3$, T, U, V, W and X are as defined in formula (I) and the group (-$Y^2$—$CH_2$—) represents Y as defined in formula (I);

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

In process (a), the reaction is performed by treating an amine of formula (III) with an electrophile of formula (II) in an inert solvent. Suitable leaving groups $L^1$ include sulfonate, trifluorosulfonate, mesylate, tosylate, and halides selected from the group chloride, bromide or iodide. The reaction is generally performed in the presence of a base. This base can be either an excess of the amine nucleophile or can be an additive to the reaction mixture. Potential basic additives are metal carbonates, especially alkali metal carbonates such as caesium carbonate, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols.

In process (b), the reductive amination reaction generally takes place under conditions which will be known to persons skilled in the art. For example, treatment of an aldehyde (IV) with an amine (III) in the presence of a reducing agent in an inert solvent. Suitable reducing systems include catalytic hydrogenation or borane and derivatives thereof. A partial list of such reagents can be found in "Advanced Organic Chemistry", J. March (1985) $3^{rd}$ Edition on page 799.

In processes (c) and (d), the reaction will take place either using an appropriate palladium source such as palladium (II) acetate in the presence of a suitable phosphine ligand, or using a copper salt under Ullmann coupling conditions. Suitable conditions for such coupling reactions are referred to in the article by Buchwald et al, *J. Amer. Chem. Soc.*, 1999, 121, 43694378.

Alternatively, in process (c), the reaction will take place under conditions similar to those described above for process (a).

In process (e), the reduction of the cyano group will take place under conditions that will be generally well known to the man skilled in the art. These include the use of diborane or of Raney nickel in the presence of hydrogen and a base such as ammonia, as the reducing agent.

It will be apparent to a person skilled in the art that in the above processes it may be desirable to protect an amine or other potentially reactive group. Suitable protecting groups and details of processes for adding and removing such groups may be found by reference to the standard text "Protective Groups in Organic Synthesis", 3rd Edition (1999) by Greene and Wuts.

In one particular embodiment, amine groups are protected as carbamate derivatives, for example, as t-butyloxycarbamates.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Certain novel intermediates of formulae (II), (IV) and (IX) form another aspect of the invention.

In general, compounds of formulae (II), (IV) and (IX) may be prepared using similar types of reactions to those described above for the preparation of compounds of formula (I).

Compounds of formula (I) wherein X represents $S(O)_n$ and n is 1 or 2 may be prepared by oxidation of a corresponding compound of formula (I) wherein n is 0. The reaction is performed by reacting a compound of formula (I) wherein X is S with a suitable oxidising agent in an inert solvent. The reaction can be controlled so as to afford either the corresponding sulfoxide (X=SO) or sulfone (X=SO$_2$) by correct choice of the oxidising reagent used, the quantity of reagent used and the reaction conditions employed. Suitable oxidising reagents and reaction conditions are given in "Advanced Organic Chemistry", J. March (1985) $3^{rd}$ Edition on pages 1089-1090.

Compounds of formulae (III), (V), (VI), (VII) and (VIII) are either known or may be prepared by conventional methods known per se.

Intermediate compounds may be used in protected form. Protecting groups and details of processes for their removal may be found by reference to the standard text "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts, are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. Alternatively or additionally, they may have utility as inhibitors of the neuronal isoform of the enzyme nitric oxide synthase and as such are predicted to have utility in the treatment of CNS disorders.

The compounds and their pharmaceutically acceptable salts are indicated for use in the treatment or prophylaxis of diseases or conditions in which synthesis or oversynthesis of nitric oxide forms a contributory part. In one aspect, the compounds are indicated for use in the treatment of inflammatory conditions in mammals including man. In another aspect, the compounds are indicated for use in the treatment of CNS disorders in mammals including man.

As used herein, reference to any of the terms "disease", "condition" and "disorder" is to be taken as a reference to all three terms.

Diseases, conditions and disorders that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis, glaucoma and conjunctivitis;

lung disorders in which inflammation is involved, for example, asthma, bronchitis, chronic obstructive pulmonary disease, pigeon fancier's disease, farmer's lung, acute respiratory distress syndrome;

bacteraemia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

The compounds may also be useful in the treatment of cancer.

The compounds may also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease, pain and cancer.

The compounds of formula (I) and their pharmaceutically acceptable salts may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, muscular dystrophy, Korsakoff's disease, imbecility relating to a cerebral vessel disorder, sleeping disorders, schizophrenia, depression, pain, autism, seasonal affective disorder, jet-lag, depression or other symptoms associated with Premenstrual Syndrome (PMS), anxiety and septic shock. Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointestinal motility disorders and in the induction of labour.

We are particularly interested in the conditions stroke, Alzheimer's disease, Parkinson's disease, multiple sclerosis, schizophrenia, migraine, septic shock and pain; more particularly migraine.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, inhalation-intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

The invention further provides a pharmaceutical composition comprising a compound of formula (I), or a pharmaceutically acceptable salt thereof, in admixture with a pharmaceutically acceptable adjuvant, diluent or carrier. There is also provided a process for the preparation of such a pharmaceutical composition which comprises mixing the ingredients.

The compounds of formula (I), and pharmaceutically acceptable derivatives thereof, may also be advantageously used in combination with a COX inhibitor, more particularly in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

The following abbreviations are used:

CDI 1,1'-carbonyldiimidazole;
DMF N,N-dimethylformamide;
DMSO dimethylsulphoxide;
THF tetrahydrofuran.

Unless otherwise stated, chromatography was carried out on silica gel columns using gradients of ethyl acetate in hexanes as eluent.

Preparation 1

[(3-Hydroxyphenyl)methyl]carbamic acid tert-butyl ester 3-(Aminomethyl)phenol hydrobromide (4.2 g, 20.6 mmol) was dissolved in ethyl alcohol (80 ml) and triethylamine (3.5 ml, 25 mmol) was added followed by di-tert-butyl dicarbonate (4.8 g, 22 mmol) and the reaction mixture stirred for 4 h. The solvent was removed by evaporation, water added and the mixture extracted with ethyl acetate and dried over magnesium sulphate. The solvent was evaporated and the residue purified by flash chromatography using 50% ethyl acetate/isohexane as eluent to give the title compound as a colourless solid (3.8 g, 83%).

MS (+CI) 124 [M−100+H]$^+$.

EXAMPLE 1

3-(5-Methoxy-2-nitrophenoxy)benzenemethanamine hydrochloride (2-Fluoro-4-methoxy)nitrobenzene (0.342 g), [(3-hydroxyphenyl)methyl]carbamic acid tert-butyl ester (0.45 g) and anhydrous potassium carbonate (0.28 g) were heated with stirring in dry DMF (15 ml) at 80° C. for 20 h. The reaction mixture was cooled, partitioned between ethyl acetate and water, the organic layer separated, washed five times with water, then brine and dried ($MgSO_4$). The solvent was evaporated and the residue eluted down a Biotage column using isohexane/ether (4:1) as eluent to give a viscous oil (the tert-butyl ester of the product). This material was stirred with 4M hydrogen chloride in dioxane (15 ml) for 2 h, concentrated to dryness and the residue triturated with ether to give after collection by filtration and drying, a cream solid (0.5 g, 80%).

MS (+CI) 275 $[M+H]^+$.

300 MHz $^1H$ NMR ($d_6$-DMSO) 8.37 (1H, br.s), 8.17 (1H, d), 7.46 (1H, t), 7.30 (1H, d), 7.23 (1H, d), 7.08 (1H, d of d), 6.98 (1H, d of d), 6.63 (1H, d), 4.03 (2H, br, d), 3.83 (3H, s).

EXAMPLE 2

3-(5-Methyl-2-nitrophenoxy)benzenemethanamine hydrochloride

The title compound was prepared as a yellow solid using the method of Example 1 and starting with 3-fluoro-4-nitrotoluene.

MS (+CI) 259 $[M+H]^+$.

300 MHz $^1H$ NMR ($d_6$-DMSO) 8.42 (3H, br.s), 8.02 (1H, d), 7.46 (1H, t), 7.31 (1H, d), 7.22 (2H, m), 7.05 (1H, d of d), 7.0 (1H, d), 4.03 (2H, d), 2.36 (3H, s).

EXAMPLE 3

3-(5-Chloro-2-nitrophenoxy)benzenemethanamine hydrochloride

The title compound was prepared as a yellow solid using the method of Example 1 and starting from 2,4-dichloronitrobenzene.

MS (+CI) 279 $[M+H]^+$.

400 MHz $^1H$ NMR ($d_6$-DMSO) 8.34 (2H, br.s), 8.17 (1H, d), 7.55-7.49 (2H, m), 7.37 (1H, d), 7.30 (1H, s), 7.20-7.11 (2H, m), 4.05 (2H, s).

EXAMPLE 4

3-(5-Fluoro-2-nitrophenoxy)benzenemethanamine hydrochloride

The title compound was prepared as a yellow solid using the method of Example 1 and starting from 2,4-difluoronitrobenzene.

MS (+CI) 263 $[M+H]^+$.

300 MHz $^1H$ NMR ($d_6$-DMSO) 8.36 (2H, br.s), 8.24 (1H, dd), 7.45 (1H, t), 7.38 (1H, d), 7.36-7.24 (2H, m), 7.20 (1H, dd), 7.02 (1H, dd), 4.05 (2H, d).

EXAMPLE 5

3-(5-Methylamino-2-nitrophenoxy)benzenemethanamine hydrochloride 3-(5-Fluoro-2-nitrophenoxy)benzenemethanamine tert-butyl ester (prepared by the method of Example 4 but omitting the final treatment with hydrogen chloride) (92 mg) was stirred with methylamine (2M in THF, 2.5 ml) for 16 h at room temperature. Purification by flash column chromatography eluting with 25% ethyl acetate/hexane gave the tert-butyl ester of the title compound which was dissolved in 4N hydrogen chloride in dioxane and stirred for 16 h. The resulting yellow solid was filtered off to give the product.

MS (+CI) 274 $[M+H]^+$.

300 MHz $^1H$ NMR ($d_6$-DMSO) 8.26 (2H, br.s), 8.03 (1H, d), 7.42 (1H, t), 7.22 (1H, d), 7.14 (1H, s), 6.99 (1H, dd), 6.49 (1H, dd), 6.13 (1H, d), 4.02 (2H, q), 2,72 (3H, s).

EXAMPLE 6

3-(5-Methoxy-2-nitrophenylthio)benzenemethanamine hydrochloride a) 3-[(5-Methoxy-2-nitrophenyl)thio]benzoic acid (2-Fluoro-4-methoxy)nitrobenzene (0.86 g, 5 mmol), 3-mercaptobenzoic acid (0.77 g, 5 mmol) and anhydrous potassium carbonate (1.38 g, 10 mmol) in dry DMF (25 ml) were heated at 80° C. with stirring for 3 h. The reaction mixture was concentrated to low volume, diluted with water (100 ml), washed with ethyl acetate, the aqueous layer was acidified and the precipitated product collected by filtration and dried to give a yellow solid (1.16 g).

MS (−CI) 304 $[M-H]^-$.

b) 3-[(5-Methoxy-2-nitrophenyl)thio]benzamide

3-[(5-Methoxy-2-nitrophenyl)thio]benzoic acid (0.89 g, 2.88 mmol) in dichloromethane (30 ml) was treated with oxalyl chloride (0.51 ml, 5.8 mmol) followed by dry DMF (2 drops) and stirred for 20 h. The solvent and excess reagent were removed by evaporation, the residual solid dissolved in dry dioxane (50 ml), cooled in ice and saturated with ammonia gas. The ammonium chloride was filtered off and the filtrate evaporated. The residual solid was triturated with ether to give a pale yellow solid (0.72 g).

MS (+CI) 305 $[M+1]^+$.

c) 3-(5-Methoxy-2-nitrophenylthio)benzenemethanamine hydrochloride

3-[(5-Methoxy-2-nitrophenyl)thio]benzamide (0.6 g, 1.97 mmol) in THF (25 ml) was treated with 1M borane in THF (10 ml, 9.86 mmol) at 0° C. with stirring. The clear solution was heated under reflux with stirring for 24 h under nitrogen. The reaction mixture was cooled, treated with 5N hydrochloric acid (20 ml) and stirred for 1 h. The mixture was cooled to 0° C., basified with solid potassium hydroxide and extracted with ethyl acetate. The extracts were washed with brine and dried ($MgSO_4$). The solvent was evaporated and the residue eluted down a silica column using 5% methanol/dichloromethane as eluent to give a yellow solid (0.414 g, 72%).

MS (+CI) 291 $[M+H]^+$.

300 MHz $^1H$ NMR ($d_6$-DMSO) 8.30 (1H, d), 7.63 (1H, d), 7.45-7.56 (3H, m), 6.95 (1H, d of d), 6.16 (1H, d), 3.77 (2H, s), 3.66 (3H, s), 1.98 (2H, br.s).

EXAMPLE 7

2-[3-(Aminomethyl)phenoxy]-4-chlorobenzonitrile hydrochloride a) 4-Chloro-2-(3-aminomethyl-2-phenoxy)benzoic acid hydrochloride 2,4-Dichlorobenzoic acid (191 mg) and 1,1-dimethylethyl [(3-hydroxyphenyl)methyl]carbamate (249 mg) were dissolved in methanol (15 ml) and treated with 25% sodium methoxide in methanol (0.26 ml). The reaction mixture was evaporated to dryness, treated with dry dioxan (10 ml) followed by copper (1) chloride (10 mg) and tris[2-(2-methoxyethoxy)ethyl]amine (TDA-1, 0.032 ml) and heated under reflux with stirring for 8 h. The reaction was left to stand over the weekend, concentrated to dryness, dissolved in water, and washed with ethyl acetate. The aqueous layer was acidified with dilute hydrochloric acid and extracted into ethyl acetate which was dried ($MgSO_4$). The solvent was evaporated and the residual viscous oil was stirred with 4M hydrogen chloride in dioxan (10 ml) for 1 h. The precipitated solid was collected by filtration, washed with ether and dried to give the sub-title compound (95 mg) as a colourless solid.

$^1$H NMR 300 MHz ($d_6$-DMSO) 13.1 (1H, br.s), 8.37 (3H, br.s), 7.89 (1H, d), 7.44 (1H, t), 7.36 (1H, dd), 7.28 (1H, d), 7.19 (1H, d), 7.00 (2H, m), 4.02 (2H, d).

MS APCI+ve$^m$/z 278 ([M+H]$^+$).

b) 2-[3-(Aminomethyl)phenoxy]-4-chlorobenzonitrile hydrochloride

The product from step (a) (542 mg) in acetonitrile (20 ml) was treated with CDI (235 mg) and stirred for 2 h. The solution was cooled in ice, saturated with ammonia gas and stirred for 1 h. The reaction mixture was diluted with dichloromethane, washed with water, aqueous sodium bicarbonate solution, then brine and dried ($MgSO_4$). The solvent was evaporated to give 1,1-dimethylethyl {[3-[2-(aminocarbonyl)-5-chlorophenoxy]phenyl]methyl}carbamate (490 mg) as a gum.

The above amide (490 mg) and triethylamine (0.37 ml) in dichloromethane (10 ml) was treated dropwise with trichloroacetyl chloride (0.16 ml) in dichloromethane (10 ml) with stirring at 0-5° C. After 0.5 h, more trichloroacetyl chloride (0.8 ml) was added and stirring continued for 0.25 h. The reaction mixture was washed with aqueous sodium bicarbonate solution, dilute hydrochloric acid, water, then brine, and dried ($MgSO_4$). The solvent was evaporated and the residue was purified by chromatography (silica gel, dichloromethane as eluent) to give 1,1-dimethylethyl {[3-(5-chloro-2-cyanophenoxy)phenyl]methyl}carbamate (240 mg) as a colourless solid.

MS APCI+ve$^m$/z 259/261([M+H]$^+$-Boc).

The above cyano compound (240 mg) was stirred with 4M hydrogen chloride in dioxan (10 ml) for 1 h and the product which had precipitated was collected by filtration, washed with ether and dried to give the title compound (122 mg) as a colourless solid.

MS APCI+ve$^m$/z 259 ([M+H]$^+$).

$^1$H NMR 300 MHz ($d_6$-DMSO) 8.41 (3H, br.s), 8.0 (1H, d), 7.55 (1H, t), 7.43 (2H, dd), 7.36 (1H, m), 7.25 (1H, dd), 6.99 (1H, d), 4.07 (2H, br s).

EXAMPLE 8

4-Chloro-2-[3-hydroxy-5-[(methylamino)methyl]phenoxy]benzonitrile a) 4-Chloro-2-[3-hydroxy-5-(hydroxymethyl)phenoxy]benzonitrile

To a stirred solution of cesium carbonate (11.62 g) in dry DMF (70 ml) was added 5-(hydroxymethyl)-1,3-benzenediol (5 g) followed by 4-chloro-2-fluorobenzonitrile (5 g). The mixture was then stirred and heated at 120° C. for 3 h. The cooled mixture was then poured into water (200 ml) and made acidic by the addition of 2M aqueous hydrochloric acid. The products were extracted into ethyl acetate (3×150 ml), and the combined extracts were washed with 10% aqueous potassium carbonate solution (100 ml). The organic extract was collected, dried ($MgSO_4$) and concentrated to dryness. Diethyl ether was added to the residue and the mixture filtered. The filtrate was concentrated to dryness and the residue purified by chromatography (silica, 70% diethyl ether/isohexane) to afford, after trituration with diethyl ether, the sub-title compound (800 mg).

300 MHz $^1$H NMR ($d_6$-DMSO) 9.80 (1H, s), 7.95 (1H, d), 7.38 (1H, dd), 6.98 (1H, d), 6.7 (1H, s), 6.52 (1H, s), 6.4 (1H, t), 5.22 (1H, t), 4.43 (2H, d).

b) 4-Chloro-2-[3-hydroxy-5-[(methylamino)methyl]phenoxy]benzonitrile

The product from step (a) (0.5 g) was treated with thionyl chloride (20 ml) and the mixture stirred at room temperature for 1.5 h. The excess reagent was removed under reduced pressure and the residual oil dissolved in methanol (20 ml). The solution was treated with excess methylamine and stirred at room temperature for 1 h. The solvent was removed under reduced pressure and the purified by chromatography (silica, 10% 7M ammonia in methanol/dichloromethane) to afford the title compound (195 mg) as a colourless solid.

MS (+CI) 289 [M+H]$^-$.

300 MHz $^1$H NMR ($d_6$-DMSO) 7.94 (1H, d), 7.38 (1H, dd), 6.97 (1H, d), 6.67 (1H, m), 6.55 (1H, s), 6.4 (1H, t), 3.56 (2H, s), 2.23 (3H, s).

EXAMPLE 9

4-Chloro-2-[3-methoxy-5-[(methylamino)methyl]phenoxy]benzonitrile oxalate a) 4-Chloro-2-(3-formyl-5-hydroxyphenoxy)benzonitrile

Sodium hydride (502 mg, 60% in mineral oil) was added portionwise to 4-chloro-2-fluorobenzonitrile (2.04 g) and 3,5-dihydroxybenzaldehyde (1.81 g) in DMF and the solution heated to 80° C. for 16 h. The cooled solution was diluted with water, acidified with concentrated hydrochloric acid, extracted twice with ethyl acetate, the extracts dried over sodium sulphate and evaporated. Purification by chromatography gave the sub-title compound as a white solid (0.83 g).

300 MHz $^1$H NMR ($CDCl_3$) 9.92 (1H, s), 7.63 (1H, d), 7.23-7.22 (2H, m), 7.13 (1H, m) 6.94 (1H, s), 6.88 (1H, t), 5.52 (1H, br.s).

b) 4-Chloro-2-(3-formyl-5-methoxyphenoxy)benzonitrile

4-Chloro-2-(3-formyl-5-hydroxyphenoxy)benzonitrile (0.20 g, 0.75 mmol) in DMF (5 ml) was treated with sodium hydride (60% in mineral oil, 30 mg, 0.78 mmol) followed after 10 min by methyl iodide (0.1 ml). After 16 h, a further amount of sodium hydride (8 mg) and methyl iodide (0.1 ml) were added. After 3 h, the mixture was diluted with water, extracted with ethyl acetate, the extracts washed with water, dried over sodium sulphate and evaporated to give the sub-title compound as a pale yellow solid (213 mg).

300 MHz $^1$H NMR (CDCl$_3$) 9.95 (1H, s), 7.63 (1H, d), 7.31-7.26 (1H, m), 7.22-7.15 (2H, m), 6.93-6.91 (2H, m), 3.90 (3H, s).

c) 4-Chloro-2-[3-methoxy-5-[(methylamino)methyl]phenoxy]benzonitrile oxalate 4-Chloro-2-(3-formyl-5-methoxyphenoxy)benzonitrile (210 mg) was stirred in 40% aqueous methylamine (2 ml) and methanol (2 ml) for 16 h. The solution was evaporated, azeotroping with toluene. The residue was dissolved in ethanol and sodium borohydride (39 mg) added portionwise and stirred for 2 h. The mixture was diluted with water, extracted twice with ethyl acetate, the combined extracts dried over sodium sulphate and evaporated. Oxalic acid (58 mg) in ethanol was added and the title compound (187 mg) was collected by filtration as a white solid.

MS (+CI) 303 [M+H]$^-$.

400 MHz $^1$H NMR (d$_6$-DMSO) 7.99 (1H, d), 7.45 (1H, d), 7.43 (1H, d), 7.07 (1H, d), 7.01 (1H, br.s), 6.91 (1H, t), 6.85 (1H, br.s), 4.09 (2H, s), 3.81 (3H, s), 2.55 (3H, s).

EXAMPLE 10

4-Chloro-2-(3-methylaminomethyl-phenoxy)-benzonitrile fumarate a) 4-Chloro-2-(3-formyl-phenoxy)-benzonitrile

4-Chloro-2-fluorobenzonitrile (1.00 g, 6.43 mmol), 3-hydroxybenzaldehyde (0.79 g, 6.43 mmol) and cesium carbonate (2.09 g, 6.43 mmol) were heated with stirring in dry DMF (5 ml) at 50° C. for 23 h. The reaction mixture was cooled, poured into water and extracted with ethyl acetate. The ethyl acetate layer was separated, washed with water (3×), 10% aqueous sodium carbonate (2×), water, brine, and dried over MgSO$_4$. After filtration, the solvent was removed in vacuo to yield 4-chloro-2-(3-formyl-phenoxy)-benzonitrile (1.52 g, 91%) as a yellow oil which solidified.

$^1$H NMR (300 MHz, CDCl$_3$) 10.02 (1H, s), 7.78 (1H, d), 7.67-7.56 (3H, m), 7.40 (1H, dd), 7.20 (1H, dd), 6.87 (1H, d).

b) 4-Chloro-2-(3-methylaminomethyl-phenoxy)-benzonitrile fumarate

4-Chloro-2-(3-formyl-phenoxy)-benzonitrile (0.52 g, 2.02 mmol), methylamine (2M in methanol, 1.0 ml, 2.0 mmol) and sodium cyanoborohydride (0.14 g, 2.2 mmol) were stirred at ambient temperature in a 1% acetic acid/methanol solution (30 ml) for 18 h. The solvent was removed in vacuo. The residue was treated with 10% aqueous sodium carbonate and extracted with ethyl acetate. The ethyl acetate layer was separated and washed with water, brine and dried over MgSO$_4$. After filtration, fumaric acid (0.23 g, 2.0 mmol) was added to the filtrate and the solvent removed in vacuo. The residue was triturated with ethyl acetate overnight, filtered and dried to give 4-chloro-2-(3-methylaminomethyl-phenoxy)-benzonitrile fumarate (454 mg, 58%) as a white solid.

MS (APCI+) 273/275 [M+1]$^+$.

$^1$H NMR (300 MHz, d$_6$-DMSO) 7.97 (1H, d), 7.52 (1H, t), 7.41 (1H, dd), 7.37 (1H, br d), 7.31 (1H, br s), 7.22 (1H, dd), 6.99 (1H, d), 6.47 (2H, s), 4.01 (2H, s), 2.45 (3H, s).

EXAMPLE 11

4-Chloro-2-(4-methoxy-3-methylaminomethyl-phenoxy)-benzonitrile fumarate a) 5-Hydroxy-2-methoxybenzaldehyde

Concentrated sulfuric acid (110 ml) was added to 2,5-dimethoxybenzaldehyde (20.17 g, 0.121 mol) with cooling in an ice water bath. The resulting red suspension was stirred at 50° C. for 46 h. The reaction contents were poured over ice and extracted with diethyl ether. The ether layer was extracted with 1N sodium hydroxide (200 ml). The basic extract was acidified by addition of 3N hydrochloric acid and extracted with diethyl ether (2×). The ether extracts were combined and dried over MgSO$_4$. After filtration, the solvent was removed in vacuo to give 5-hydroxy-2-methoxybenzaldehyde (5.85 g, 32%) as an orange solid.

MS (APCI+) 153 [M+I]$^+$.

$^1$H NMR (300 MHz, CDCl$_3$) 10.40 (1H, s), 7.37 (1H, d), 7.13 (1H, dd), 6.91 (1H, d), 5.88 (1H, br s), 3.89 (3H, s).

b) 4-Chloro-2-(3-formyl-4-methoxy-phenoxy)-benzonitrile

4-Chloro-2-fluorobenzonitrile (0.60 g, 3.9 mmol), 5-hydroxy-2-methoxybenzaldehyde (0.59 g, 3.9 mmol) and cesium carbonate (1.26 g, 3.9 mmol) were heated with stirring in dry DMF (4 ml) at 50° C. for 17 h. The reaction mixture was cooled, poured into water and extracted with ethyl acetate. The ethyl acetate layer was separated, washed with water, 10% aqueous sodium carbonate (2×), water (2×), brine and dried over MgSO$_4$. After filtration, the solvent was removed in vacuo to yield 4-chloro-2-(3-formyl-4-methoxy-phenoxy)-benzonitrile (1.01 g, 90%) as a yellow solid.

$^1$H NMR (300 MHz, d$_6$-DMSO) 10.33 (1H, s), 7.96 (1H, d), 7.61 (1H, dd), 7.47 (1H, d), 7.39 (1H, br s), 7.36 (1H, br s), 6.94 (1H, d), 3.97 (3H, s).

c) 4-Chloro-2-(4-methoxy-3-methylaminomethyl-phenoxy)-benzonitrile fumarate 4-Chloro-2-(3-formyl-4-methoxy-phenoxy)-benzonitrile (1.00 g, 3.48 mmol), methylamine (2M in methanol, 5.2 ml, 10.4 mmol) and sodium cyanoborohydride (0.24 g, 3.8 mmol) were stirred at ambient temperature in a 1% acetic acid/methanol solution (75 ml) for 18 h. The solvent was removed in vacuo. The residue was treated with 10% aqueous sodium carbonate and extracted with ethyl acetate. The ethyl acetate layer was separated and washed with water, brine and dried over MgSO$_4$. After filtration, fumaric acid (0.40 g, 3.4 mmol) was added to the filtrate and the solvent removed in vacuo. The residue was triturated with ethyl acetate overnight, filtered and dried to give 4-chloro-2-(3-methylaminomethyl-phenoxy)-benzonitrile fumarate (892 mg, 61%) as a white solid.

MS (APCI+) 303/305 [M+1]$^+$.

¹H NMR (300 MHz, d₆-DMSO) 7.94 (1H, d), 7.37-7.23 (3H, m), 7.15 (1H, d), 6.82 (1H, br s), 6.46 (2H, s), 3.94 (2H, s), 3.86 (3H, s), 2.45 (3H, s).

EXAMPLE 12

4-Chloro-2-(2-methoxy-3-methylaminomethyl-phenoxy)-benzonitrile fumarate a) 3-Hydroxy-2-methoxy-benzaldehyde 2,3-Dihydroxybenzaldehyde (1.00 g, 7.24 mmol), potassium carbonate (1.00 g, 7.24 mmol) and iodomethane (0.59 ml, 1.34 g, 9.4 mmol) in dry DMF (10 ml) were stirred at ambient temperature for 19 h. The reaction mixture was cooled, poured into water and extracted with ethyl acetate. The ethyl acetate layer was extracted with 1N aqueous sodium hydroxide (3×). The basic extracts were combined and acidified by addition of 3N hydrochloric acid, then extracted with ethyl acetate. The ethyl acetate layer was washed with water (4×), brine and dried over MgSO₄. After filtration, the solvent was removed in vacuo to yield 3-hydroxy-2-methoxy-benzaldehyde (0.68 g, 62%) as a yellowish-tan solid.

MS (APCI+) 153 [M+1]⁺.

¹H NMR (300 MHz, CDCl₃) 10.27 (1H, s), 7.37 (1H, dd), 7.26-7.21 (1H, m), 7.15 (1H, d), 5.80 (1H, s), 3.97 (3H, s).

b) 4-Chloro-2-(3-formyl-2-methoxy-phenoxy)-benzonitrile

4-Chloro-2-fluorobenzonitrile (0.65 g, 4.2 mmol), 3-hydroxy-2-methoxybenzaldehyde (0.64 g, 4.2 mmol) and cesium carbonate (1.37 g, 4.2 mmol) were heated with stirring in dry DMF (4 ml) at 50° C. for 18 h. The reaction mixture was cooled, poured into water and extracted with ethyl acetate. The ethyl acetate layer was separated, washed with water (2×), 10% aqueous sodium carbonate (2×), water and brine and dried over MgSO₄. After filtration, the solvent was removed in vacuo to yield 4-chloro-2-(3-formyl-4-methoxy-phenoxy)-benzonitrile (1.09 g, 90%) as a yellow-orange solid.

¹H NMR (300 MHz, CDCl₃) 10.41 (1H, s), 7.80 (1H, dd), 7.62 (1H, d), 7.40 (1H, dd), 7.30 (1H, d), 7.15 (1H, dd), 6.69 (1H, d), 4.01 (3H, s).

c) 4-Chloro-2-(2-methoxy-3-methylaminomethyl-phenoxy)-benzonitrile fumarate

4-Chloro-2-(3-formyl-2-methoxy-phenoxy)-benzonitrile (0.52 g, 1.8 mmol), methylamine (2M in methanol, 2.7 ml, 5.4 mmol) and sodium cyanoborohydride (0.13 g, 2.1 mmol) were stirred at ambient temperature in a 1% acetic acid/methanol solution (70 ml) for 20 h. The solvent was removed in vacuo. The residue was treated with 10% aqueous sodium carbonate and extracted with ethyl acetate. Fumaric acid (0.21 g, 1.8 mmol) was added to the separated ethyl acetate layer and the solvent removed in vacuo. The residue was triturated with ethyl acetate overnight, filtered and dried to give 4-chloro-2-(2-methoxy-3-methylaminomethyl-phenoxy)-benzonitrile fumarate (583 mg, 77%) as a white solid.

MS (APCI+) 303/305 [M+1]⁺.

¹H NMR (300 MHz, d₆-DMSO) 7.97 (1H, d), 7.45 (1H, dd), 7.36 (1H, dd), 7.27-7.23 (2H, m), 6.78 (1H, d), 6.49 (2H, s), 3.95 (2H, s), 3.79 (3H, s), 2.45 (3H, s).

EXAMPLE 13

4-Chloro-2-(2-methoxy-4-methylaminomethyl-phenoxy)-benzonitrile fumarate a) 4-Chloro-2-(4-formyl-2-methoxy-phenoxy)-benzonitrile

4-Chloro-2-fluorobenzonitrile (0.60 g, 3.9 mmol), vanillin (0.59 g, 3.9 mmol) and cesium carbonate (1.26 g, 3.9 mmol) were heated with stirring in dry DMF (4 ml) at 50° C. for 22 h. The reaction mixture was cooled, poured into water and extracted with ethyl acetate. The ethyl acetate layer was separated, washed with water, 10% aqueous sodium carbonate (2×), water (2×), brine, and dried over MgSO₄. After filtration, the solvent was removed in vacuo to yield 4-chloro-2-(4-formyl-2-methoxy-phenoxy)-benzonitrile (0.98 g, 88%) as an off-white solid.

¹H NMR (300 MHz, CDCl₃) 9.99 (1H, s), 7.61-7.51 (3H, m), 7.27 (1H, d), 7.14 (1H, dd), 6.70 (1H, d), 3.88 (3H, s).

b) 4-Chloro-2-(2-methoxy-4-methylaminomethyl-phenoxy)-benzonitrile fumarate

4-Chloro-2-(4-formyl-2-methoxy-phenoxy)-benzonitrile (0.98 g, 3.4 mmol), methylamine (2M in methanol, 5.1 ml, 10.2 mmol) and sodium cyanoborohydride (0.24 g, 3.8 mmol) were stirred at ambient temperature in a 1% acetic acid/methanol solution (125 ml) for 20 h. The solvent was removed in vacuo. The residue was treated with 10% aqueous sodium carbonate and extracted with ethyl acetate. Fumaric acid (0.41 g, 3.5 mmol) was added to the separated ethyl acetate layer and the solvent removed in vacuo. The residue was triturated with ethyl acetate overnight, filtered and dried to give 4-chloro-2-(2-methoxy-4-methylaminomethyl-phenoxy)-benzonitrile fumarate (1.14 g, 80%) as a white solid.

MS (APCI+) 303/305 [M+1]⁺.

H NMR (300 MHz, d₆-DMSO) 7.92 (1H, d), 7.37 (1H, br s), 7.31 (1H, dd), 7.26 (1H, d), 7.09 (1H, d), 6.62 (1H, d), 6.49 (2H, s), 3.94 (2H, s), 3.76 (3H, s), 2.45 (3H, s).

EXAMPLE 14

4-Chloro-2-(3-methoxy-4-methylaminomethyl-phenoxy)-benzonitrile fumarate a) 4-Chloro-2-(4-formyl-3-methoxy-phenoxy)-benzonitrile

4-Chloro-2-fluorobenzonitrile (0.60 g, 3.9 mmol), 4-hydroxy-2-methoxybenzaldehyde (0.59 g, 3.9 mmol) and cesium carbonate (1.26 g, 3.9 mmol) were heated with stirring in dry DMF (4 ml) at 50° C. for 21 h. The reaction mixture was cooled, poured into water and extracted with ethyl acetate. The ethyl acetate layer was separated, washed with water, 10% aqueous sodium carbonate (2×), water (2×), brine, and dried over magnesium sulphate. After filtration, the solvent was removed in vacuo to yield 4-chloro-2-(4-formyl-3-methoxy-phenoxy)-benzonitrile (0.93 g, 83%) as an orange solid.

¹H NMR (300 MHz, CDCl₃) 10.40 (1H, s), 7.89 (1H, d), 7.64 (1H, d), 7.24 (1H, dd), 7.02 (1H, d), 6.74 (1H, d), 6.63 (1H, dd), 3.93 (3H, s).

b) 4-Chloro-2-(3-methoxy-4-methylaminomethyl-phenoxy)-benzonitrile fumarate

4-Chloro-2-(4-formyl-3-methoxy-phenoxy)-benzonitrile (0.93 g, 3.2 mmol), methylamine (2M in methanol, 4.8 ml, 9.6 mmol) and sodium cyanoborohydride (0.22 g, 3.6 mmol) were stirred at ambient temperature in a 1% acetic acid/methanol solution (125 ml) for 20 h. The solvent was removed in vacuo. The residue was treated with 10% aqueous sodium carbonate and extracted with ethyl acetate. Fumaric acid (0.40 g, 3.4 mmol) was added to the separated ethyl acetate layer and the solvent removed in vacuo. The residue was triturated with ethyl acetate overnight, filtered and dried to give 4-chloro-2-(2-methoxy-4-methylaminomethyl-phenoxy)-benzonitrile fumarate (782 mg, 58%) as a white solid.

MS (APCI+) 303/305 [M+1]$^+$.

$^1$H NMR (300 MHz, d$_6$-DMSO) 7.96 (1H, d), 7.46 (1H, d), 7.39 (1H, dd), 6.99-6.95 (2H, m), 6.76 (1H, dd), 6.47 (2H, s), 3.91 (2H, s), 3.83 (3H, s), 2.44 (3H, s).

EXAMPLE 15

2-(4-Bromo-3-methylaminomethyl-phenoxy)-4-trifluoromethyl-benzonitrile fumarate a) 2-(4-Bromo-3-formyl-phenoxy)-4-trifluoromethyl-benzonitrile

A flask was charged with 2-fluoro-4-(triflouromethyl)benzonitrile (3.78 g, 2 mmol), 2-bromo-4-hydroxy-benzaldehyde (4.02 g, 2 mmol), cesium carbonate (6.5 g, 2 mmol) and DMF (40 ml). The mixture was stirred overnight at 40° C. The DMF was evaporated off and the residue was partitioned between ethyl acetate and 5% aqueous sodium hydrogen carbonate. The organic layer was dried with MgSO$_4$. Evaporation yielded a brown oil which solidified to give a brown solid (7.2 g, 97%).

$^1$H NMR (300 MHz, CDCl$_3$) 10.34 (1H, s), 7.84 (1H, d), 7.74 (1H, d), 7.58 (1H, d), 7.49 (1H, d), 7.25 (1H, m), 7.12 (1H, s).

b) 2-(4-Bromo-3-methylaminomethyl-phenoxy)-4-trifluoromethyl-benzonitrile fumarate To 2-(4-bromo-3-formyl-phenoxy)-4-trifluoromethyl-benzonitrile (550 mg, 1.5 mmol) was added a 2M solution of methylamine in methanol (2.25 ml, 4.5 mmol) and 1% acetic acid in methanol (25 ml). Sodium borohydride (104 mg, 1.1 eq.) was added. The reaction mixture was stirred at room temperature overnight. The methanol was evaporated off and the residue was partitioned between ethyl acetate and 5% aqueous sodium carbonate. To the organic layer was added fumaric acid (174 mg) and the solution stirred overnight. The white solid which precipitated was filtered off to yield the title compound (200 mg, 27%).

$^1$H NMR (300 MHz, d$_6$-DMSO) 8.18 (1H, d), 7.69 (2H, m), 7.43 (1H, s), 7.29 (1H, s), 7.13 (1H, m), 6.51 (2H, s), 3.88 (2H, d), 2.37 (2H, s).

MS (APCI+): 385.1, 387.09.

EXAMPLE 16

2-(2-Methylaminomethyl-biphenyl-4-yloxy)-4-trifluoromethyl-benzonitrile fumarate a) 2-(2-Formyl-biphenyl-4-yloxy)-4-trifluoromethyl-benzonitrile

To a mixture of 2-(4-bromo-3-formyl-phenoxy)-4-trifluoromethyl-benzonitrile (1.76 g, 4.76 mmol) and Pd(dba)$_3$ (21.8 mg, 5 mole %) in dimethoxyethane (15 ml) was added a solution of phenylboronic acid (609 mg, 5 mmol), triphenylphosphine (15 mg, 12 mole %) and sodium carbonate (530 mg, 5 mmol) in water (10 ml). The mixture was refluxed for 3 h. The solvent was evaporated off and the aqueous layer was extracted with dichloromethane. The extracts were dried with MgSO$_4$ and filtered through silica. Evaporation yielded a brown solid (1.73 g, 99%).

$^1$H NMR (300 MHz) (d$_6$-DMSO) 9.86 (1H, s), 8.23 (1H, d), 7.78 (1H, d), 7.51-7.65 (8H, m).

b) 2-(2-Methylaminomethyl-biphenyl-4-yloxy)-4-trifluoromethyl-benzonitrile fumarate To 2-(2-formyl-biphenyl-4-yloxy)-4-trifluoromethyl-benzonitrile (550 mg, 1.5 mmol) was added a 2M solution of methylamine in methanol (2.25 mL, 4.5 mmol) and 1% acetic acid in methanol (25 ml). Sodium borohydride (104 mg, 1.1 eq.) was added. The mixture was stirred at room temperature overnight. The methanol was evaporated off and the residue was partitioned between ethyl acetate and 5% aqueous sodium carbonate. To the organic layer was added fumaric acid (174 mg), and the solution stirred overnight. The white solid which precipitated was filtered off to yield the title compound (300 mg, 50%).

$^1$H NMR (300 MHz) (d$_6$-DMSO) 8.19 (1H, d), 7.71 (1H, d), 7.33-7.48 (8H, m), 7.25 (1H, m), 6.49 (2H, s), 3.78 (2H, s), 2.27 (3H, s).

MS (BPI Smooth/APCI+): 100% 383.5.

EXAMPLE 17

4-Chloro-2-[2-hydroxy-3-(methylaminomethyl)phenoxy]benzonitrile fumarate a) 4-Chloro-2-(3-formyl-2-hydroxyphenoxy)-benzonitrile

To a solution of 2,3-dihydroxybenzaldehyde (3.03 g, 21.9 mmol) in DMSO (25 mL) was added sodium hydride (1.97 g, 49.2 mmol, 60% suspension in mineral oil). After 45 min, 4-chloro-2-fluorobenzonitrile (3.41 g, 21.9 mmol) was added, and the reaction mixture stirred at ambient temperature for 24 h. The reaction mixture was poured into 5% ammonium chloride solution and extracted twice with ethyl acetate. The separated ethyl acetate layers were combined, washed with 1N hydrochloric acid (2×), water (2×), brine (1×), and dried over MgSO$_4$. After filtration, the solvent was removed in vacuo to give a yellow solid (5.88 g) which was triturated with hexane to yield 4-chloro-2-(3-formyl-2-hydroxyphenoxy)-benzonitrile (4.62 g, 77%) as a yellow solid.

MS (APCI+) 274 [M+1]$^+$.

$^1$H-NMR (300 MHz, CDCl$_3$): δ 11.11 (1H, s), 9.98 (1H, s), 7.62-7.54 (2H, m), 7.44 (1H, br d), 7.15-7.07 (2H, m), 6.70 (1H, d).

b) 4-Chloro-2-[2-hydroxy-3-(methylaminomethyl)phenoxy]benzonitrile fumarate 4-Chloro-2-(3-formyl-2-hydroxyphenoxy)-benzonitrile (0.30 g, 1.10 mmol), methylamine (2M in methanol, 2.5 mL, 5.0 mmol) and sodium cyanoborohydride (0.10 g, 1.6 mmol) were stirred at ambient temperature in a 1% acetic acid/methanol solution (35 mL) for 19 h. The solvent was removed in vacuo. The residue was treated with saturated sodium hydrogen carbonate solution and extracted with ethyl acetate. To the ethyl acetate layer was added fumaric acid (0.12 g, 1.03 mmol) and the solvent removed in vacuo.

The residue was triturated with ethyl acetate overnight, collected by filtration, and dried to give 4-chloro-2-[2-hydroxy-3-(methylaminomethyl)phenoxy]-benzonitrile fumarate (256 mg, 58%) as a white solid.

MS (APCI+) 289/291 [M+1]+.

$^1$H-NMR (300 MHz, $d_6$-DMSO): δ 7.88 (1H, d), 7.25 (1H, dd), 7.11 (1H, s), 7.10 (1H, s), 6.81 (1H, br t), 6.62 (1H, br s), 6.47 (2H, s), 4.00 (2H, s), 2.37 (3H, s).

EXAMPLE 18

4-Chloro-2-[2-ethoxy-3-(methylaminomethyl)phenoxy]benzonitrile fumarate a) 2-Ethoxy-3-hydroxybenzaldehyde 2,3-Dihydroxybenzaldehyde (1.12 g, 8.11 mmol), potassium carbonate (1.12 g, 8.11 mmol) and iodoethane (0.65 mL, 1.26 g, 8.11 mmol) in dry DMF (10 mL) were stirred at ambient temperature for 21 h. The reaction mixture was poured into water and extracted with diethyl ether. The ether layer was washed with water (2×), and extracted with 1N sodium hydroxide solution (3×). The basic extracts were combined and acidified by addition of 3N hydrochloric acid, then extracted with diethyl ether. The ether layer was washed with water (2×), brine (1×), and dried over MgSO$_4$. After filtration, the solvent was removed in vacuo to yield 2-ethoxy-3-hydroxybenzaldehyde (0.74 g, 55%) as an orange solid.

MS (APCI+) 166 [M+1]+.

$^1$H-NMR (300 MHz, CDCl$_3$): δ 10.26 (1H, s), 7.37 (1H, br dd), 7.24-7.11 (2H, m), 5.78 (1H, s), 4.14 (2H, q), 1.47 (3H, t).

b) 4-Chloro-2-(2-ethoxy-3-formylphenoxy)benzonitrile

4-Chloro-2-fluorobenzonitrile (0.35 g, 2.2 mmol), 2-ethoxy-3-hydroxybenzaldehyde (0.37 g, 2.2 mmol) and cesium carbonate (0.73 g, 2.2 mmol) were heated with stirring in dry DMF (4 mL) at 50° C. for 19 h. The reaction mixture was cooled, poured into water and extracted with ethyl acetate. The ethyl acetate layer was separated, washed with 1N sodium hydroxide solution (2×), water (2×), brine (1×), and dried over MgSO$_4$. After filtration, the solvent was removed in vacuo to yield 4-chloro-2-(2-ethoxy-3-formylphenoxy)benzonitrile (0.55 g, 82%) as a tan solid.

$^1$H-NMR (300 MHz, CDCl$_3$): δ 10.42 (1H, s), 7.81 (1H, dd), 7.61 (1H, d), 7.40 (1H, dd), 7.29 (1H, d), 7.14 (1H, dd), 6.68 (1H, d), 4.25 (2H, q), 1.34 (3H, t).

c) 4-Chloro-2-[2-ethoxy-3-(methylaminomethyl)phenoxy]benzonitrile fumarate

4-Chloro-2-(2-ethoxy-3-formylphenoxy)benzonitrile (0.55 g, 1.8 mmol), methylamine (2M in methanol, 3.0 mL, 6.0 mmol) and sodium cyanoborohydride (0.13 g, 2.1 mmol) were stirred at ambient temperature in a 1% acetic acid/methanol solution (55 mL) for 3 days. The solvent was removed in vacuo. The residue was treated with 10% sodium carbonate solution and extracted with ethyl acetate. Fumaric acid (0.21 g, 1.8 mmol) was added to the separated ethyl acetate layer and the solvent removed in vacuo. The residue was triturated overnight with ethyl acetate, collected by filtration, and dried to give 4-chloro-2-[2-ethoxy-3-(methylaminomethyl)phenoxy]benzonitrile fumarate (527 mg, 67%) as a white solid.

MS (APCI+) 317/319 [M+1]+.

$^1$H-NMR (300 MHz, $d_6$-DMSO): δ 7.98 (1H, d), 7.48 (1H, br d), 7.36 (1H, dd), 7.32-7.23 (2H, m), 6.74 (1H, s), 6.49 (2H, s), 4.04 (2H, q), 3.98 (2H, s), 2.46 (3H, s), 1.21 (3H, t).

EXAMPLE 19

4-Chloro-2-[2-(2-fluoroethoxy)-3-(methylaminomethyl)phenoxy]benzonitrile fumarate a) 4-Chloro-2-[2-(2-fluoroethoxy)-3-formylphenoxy]benzonitrile 4-Chloro-2-(3-formyl-2-hydroxyphenoxy)benzonitrile (0.29 g, 1.1 mmol), 1-bromo-2-fluoroethane (0.20 mL, 0.34 g, 2.7 mmol) and cesium carbonate (0.41 g, 1.3 mmol) were heated with stirring in dry DMF (5 mL) at 50° C. for 23 h. The reaction mixture was cooled, poured into 1N sodium hydroxide solution and extracted with ethyl acetate. The ethyl acetate layer was separated, washed with 1N sodium hydroxide solution (3×), water (4×), brine (1×), and dried over MgSO$_4$. After filtration, the solvent was removed in vacuo to yield 4-chloro-2-[2-(2-fluoroethoxy)-3-formylphenoxy]benzonitrile (0.35 g) as a tan solid, which was used without further purification.

$^1$H-NMR (300 MHz, CDCl$_3$): δ 10.47 (1H, s), 7.82 (1H, dd), 7.61 (1H, d), 7.40 (1H, dd), 7.31 (1H, br t), 7.16 (1H, dd), 6.71 (1H, d) 4.77-4.72 (1H, m), 4.61-4.56 (1H, m), 4.52-4.47 (1H, m), 4.42-4.37 (1H, m).

b) 4-Chloro-2-[2-(2-fluoroethoxy)-3-(methylaminomethyl)phenoxy]benzonitrile fumarate 4-Chloro-2-[2-(2-fluoroethoxy)-3-formylphenoxy]benzonitrile (0.35 g, 1.1 mmol), methylamine (2M in methanol, 3.0 mL, 6.0 mmol) and sodium cyanoborohydride (90 mg, 1.4 mmol) were stirred at ambient temperature in a 1% acetic acid/methanol solution (50 mL) for 16 h. The solvent was removed in vacuo. The residue was treated with 10% sodium carbonate solution and extracted with ethyl acetate. The ethyl acetate layer was separated and fumaric acid (0.12 g, 1.0 mmol) was added. After the solvent was removed in vacuo, the residue was triturated with ethyl acetate overnight, collected by filtration and dried to give 4-chloro-2-[2-(2-fluoroethoxy)-3-(methylaminomethyl)phenoxy]benzonitrile fumarate (194 mg, 40%) as a beige solid.

MS (APCI+) 335/337 [M+1][31].

$^1$H-NMR (300 MHz, $d_6$-DMSO): δ 7.95 (1H, d), 7.42 (1H, dd), 7.35 (1H, dd), 7.28-7.18 (2H, m), 6.76 (1H, d), 6.46 (2H, s), 4.71-4.68 (1H, m), 4.55-4.52 (1H, m), 4.28-4.24 (1H, m), 4.18-4.14 (1H, m), 3.85 (2H, s), 2.37 (3H, s).

EXAMPLE 20

4-Chloro-2-[3-methylaminomethyl-2-(2,2,2-trifluoroethoxy)phenoxy]-benzonitrile fumarate a) 4-Chloro-2-[3-formyl-2-(2,2,2-trifluoroethoxy)phenoxy]benzonitrile To a solution of 4-chloro-2-(3-formyl-2-hydroxyphenoxy)benzonitrile (0.44 g, 1.6 mmol) in dry DMSO (10 mL) was added sodium hydride (50 mg, 2.0 mmol, 95%). After stirring for 15 min at ambient temperature, 2-iodo-1,1,1-trifluoroethane (0.47 mL, 1.01 g, 4.8 mmol) was added and the mixture heated with stirring at 120° C. for 43 h. The reaction mixture was cooled, poured into 1N hydrochloric acid and extracted with diethyl ether. The ether layer was separated, washed with water (3×), brine (1×), and dried over MgSO$_4$. After filtration, the solvent was removed in vacuo to give a yellow syrup (0.51 g) which was purified by chromatography to yield 4-chloro-2-[3-formyl-2-(2,2,2-trifluoroethoxy)phenoxy]benzonitrile (0.12 g, 21%) as an off-white solid.

$^1$H-NMR (300 MHz, CDCl$_3$): δ 10.43 (1H, s), 7.84 (1H, dd), 7.65 (1H, d), 7.42-7.35 (2H, m), 7.22 (1H, dd), 6.74 (1H, br d), 4.59 (2H, q).

b) 4-Chloro-2-[3-methylaminomethyl-2-(2,2,2-trifluoroethoxy)phenoxy]-benzonitrile fumarate 4-Chloro-2-[3-formyl-2-(2,2,2-trifluoroethoxy)phenoxy]benzonitrile (0.12 g, 0.33 mmol), methylamine (33% in ethanol, 0.4 mL, 3.2 mmol) and sodium cyanoborohydride (40 mg, 0.6 mmol) were stirred at ambient temperature in a solution of glacial acetic acid (0.5 mL) in methanol (25 mL) for 18 h. The solvent was removed in vacuo. The residue was treated with 10% sodium carbonate solution and extracted with ethyl acetate. The ethyl acetate layer was separated and fumaric acid (39 mg, 0.34 mmol) was added. After the solvent was removed in vacuo, the residue was triturated with ethyl acetate overnight, collected by filtration and dried to give 4-chloro-2-[3-methylaminomethyl-2-(2,2,2-trifluoroethoxy)phenoxy]-benzonitrile fumarate (76.5 mg, 47%) as a white solid.

MS (APCI+) 371/373 [M+1]$^+$.
$^1$H-NMR (300 MHz, d$_6$-DMSO): δ 8.00 (1H, d), 7.52-7.31 (4H, m), 6.99 (1H, br s), 6.63 (2H, s), 4.77 (2H, q), 4.22 (2H, s), 2.64 (3H, s).

EXAMPLE 21

4-Chloro-2-(3-methylaminomethyl-2-propoxyphenoxy)benzonitrile fumarate a) 3-Hydroxy-2-propoxybenzaldehyde 2,3-Dihydroxybenzaldehyde (1.16 g, 8.40 mmol), potassium carbonate (1.16 g, 8.40 mmol) and 1-iodopropane (0.82 mL, 1.43 g, 8.40 mmol) in dry DMF (10 mL) were stirred at ambient temperature for 20 h. The reaction mixture was poured into water and extracted with diethyl ether. The diethyl ether layer was washed with water (2×), then extracted with 1N sodium hydroxide solution (3×). The basic extracts were combined and acidified by addition of 3N hydrochloric acid, then extracted with diethyl ether. The ether layer was washed with 10% sodium hydrogen carbonate (3×), water (1×), brine (1×), and dried over MgSO$_4$. After filtration, the solvent was removed in vacuo to yield 3-hydroxy-2-propoxybenzaldehyde (0.64 g, 42%) as a yellow solid.

MS (APCI+) 180 [M+1]$^+$.
$^1$H-NMR (300 MHz, CDCl$_3$): δ 10.28 (1H, s), 7.38 (1H, dd), 7.23 (1H, dd), 7.14 (1H, br t), 5.78 (1H, s), 4.02 (2H, t), 1.95-1.83 (2H, m), 1.08 (3H, t).

b) 4-Chloro-2-(3-formyl-2-propoxyphenoxy)benzonitrile

4-Chloro-2-fluorobenzonitrile (0.35 g, 2.2 mmol), 3-hydroxy-2-propoxybenzaldehyde (0.40 g, 2.2 mmol) and cesium carbonate (0.72 g, 2.2 mmol) were heated with stirring in dry DMF (4 mL) at 50° C. for 19 h. The reaction mixture was cooled, poured into water and extracted with ethyl acetate. The ethyl acetate layer was separated, washed with 1N sodium hydroxide solution (2×), water (1×), brine (1×), and dried over MgSO$_4$. After filtration, the solvent was removed in vacuo to yield 4-chloro-2-(3-formyl-2-propoxyphenoxy)-benzonitrile (0.69 g, 98%) as a brown oil, which was used without further purification.

$^1$H-NMR (300 MHz, CDCl$_3$): δ 10.43 (1H, s), 7.81 (1H, dd), 7.61 (1H, d), 7.40 (1H, dd), 7.29 (1H, d), 7.14 (1H, dd), 6.68 (1H, d), 4.12 (2H, t), 1.80-1.65 (2H, m), 0.93 (3H, t).

c) 4-Chloro-2-(3-methylaminomethyl-2-propoxyphenoxy)benzonitrile fumarate

4-Chloro-2-(3-formyl-2-propoxyphenoxy)benzonitrile (0.68 g, 2.2 mmol), methylamine (2M in methanol, 3.2 mL, 6.4 mmol) and sodium cyanoborohydride (0.15 g, 2.4 mmol) were stirred at ambient temperature in a 1% acetic acid/methanol solution (70 mL) for 20 h. The solvent was removed in vacuo. The residue was treated with 10% sodium carbonate solution and extracted with ethyl acetate. The ethyl acetate layer was separated and fumaric acid (250 mg, 2.2 mmol) was added. After the solvent was removed in vacuo, the residue was triturated with ethyl acetate overnight, collected by filtration, and dried to give 4-chloro-2-(3-methylaminomethyl-2-propoxyphenoxy)benzonitrile fumarate (567 mg, 59%) as a white solid.

MS (APCI+) 331/333 [M+1]$^+$.
$^1$H-NMR (300 MHz, d$_6$-DMSO): δ 7.95 (1H, d), 7.45 (1H, br dd), 7.34 (1H, d), 7.26-7.21 (2H, m), 6.71 (1H, s), 6.50 (2H, s), 3.92-3.85 (4H, m), 2.43 (3H, s), 1.68-1.53 (2H, m), 0.84 (3H, t).

EXAMPLE 22

4-Chloro-2-[2-(2-hydroxyethoxy)-3-(methylaminomethyl)phenoxy]-benzonitrile fumarate a) 4-Chloro-2-[3-formyl-2-(2-hydroxyethoxy)phenoxy]benzonitrile A solution of 4-chloro-2-(3-formyl-2-hydroxyphenoxy)benzonitrile (0.30 g, 1.1 mmol), 2-bromoethanol (0.10 mL, 0.18 g, 1.4 mmol) and cesium carbonate (0.43 g, 1.3 mmol) were heated with stirring in dry DMF (3 mL) at 50° C. After 22 h, 2-bromoethanol (0.19 mL, 0.33 g, 2.7 mmol) was added, and stirring continued for an additional 24 h at 50° C. The reaction mixture was cooled, poured into water and extracted with ethyl acetate. The ethyl acetate layer was separated, washed with 1N sodium hydroxide solution (3×), water (1×), brine (1×), and dried over MgSO$_4$. After filtration, the solvent was removed in vacuo to yield 4-chloro-2-[3-formyl-2-(2-hydroxyethoxy)phenoxy]benzonitrile (0.29 g, 83%) as a tan oil, which was used without further purification.

$^1$H-NMR (300 MHz, CDCl$_3$): δ 10.37 (1H, s), 7.79 (1H, dd), 7.62 (1H, d), 7.40 (1H, dd), 7.34 (1H, d), 7.16 (1H, dd), 6.69 (1H, d), 4.30 (2H, t), 3.90-3.82 (2H, m).

b) 4-Chloro-2-[2-(2-hydroxyethoxy)-3-(methylaminomethyl)phenoxy]-benzonitrile fumarate 4-Chloro-2-[3-formyl-2-(2-hydroxyethoxy)phenoxy]benzonitrile (0.29 g, 0.91 mmol), methylamine (2M in methanol, 2.0 mL, 4.0 mmol) and sodium cyanoborohydride (70 mg, 1.1 mmol) were stirred at ambient temperature in a 1% acetic acid/methanol solution (25 mL) for 24 h. The solvent was removed in vacuo. The residue was treated with 10% sodium carbonate solution and extracted with ethyl acetate.

The ethyl acetate layer was separated and fumaric acid (0.11 g, 0.95 mmol) was added. After the solvent was removed in vacuo, the residue was triturated with ethyl acetate overnight, collected by filtration, and dried to give 4-chloro-2-[2-(2-hydroxyethoxy)-3-methylaminomethyl)phenoxy]-benzonitrile fumarate (250 mg, 61%) as a white solid.

MS (APCI+) 333/335 [M+1]+.

$^1$H-NMR (300 MHz, $d_6$-DMSO): δ 7.96 (1H, d), 7.43-7.32 (2H, m), 7.28-7.18 (2H, m), 6.75 (1H, br s), 6.47 (2H, s), 4.04 (2H, t), 3.98 (2H, s), 3.58 (2H, t), 2.42 (3H, s).

EXAMPLE 23

4-Chloro-2-[2-ethoxy-4-(methylaminomethyl)phenoxy]benzonitrile fumarate a)
4-Chloro-2-(2-ethoxy-4-formylphenoxy)benzonitrile 4-Chloro-2-fluorobenzonitrile (0.40 g, 2.6 mmol), 3-ethoxy-4-hydroxybenzaldehyde (0.43 g, 2.6 mmol) and cesium carbonate (0.84 g, 2.6 mmol) were heated with stirring in dry DMF (4 mL) at 50° C. for 20 h. The reaction mixture was cooled, poured into water and extracted with ethyl acetate. The ethyl acetate layer was separated, washed with water (1×), 10% sodium carbonate solution (1×), 0.5N sodium hydroxide solution (1×), water (1×), brine (1×), and dried over MgSO$_4$. After filtration, the solvent was removed in vacuo to yield 4-chloro-2-(2-ethoxy-4-formylphenoxy) benzonitrile (0.67 g, 86%) as a yellow solid.

$^1$H-NMR (300 MHz, CDCl$_3$): δ 9.98 (1H, s), 7.59 (1H, d), 7.55-7.49 (2H, m), 7.30 (1H, d), 7.13 (1H, dd), 6.71 (1H, d), 4.10 (2H, q), 1.26 (3H, t).

b) 4-Chloro-2-[2-ethoxy-4-(methylaminomethyl) phenoxy]benzonitrile fumarate

4-Chloro-2-(2-ethoxy-4-formylphenoxy)benzonitrile (0.67 g, 2.2 mmol), methylamine (2M in methanol, 3.5 mL, 7.0 mmol) and sodium cyanoborohydride (0.16 g, 2.5 mmol) were stirred at ambient temperature in a 1% acetic acid/methanol solution (65 mL) for 18 h. The solvent was removed in vacuo. The residue was treated with 10% sodium carbonate solution and extracted with ethyl acetate. The ethyl acetate layer was separated and fumaric acid (0.26 g, 2.2 mmol) was added. After the solvent was removed in vacuo, the residue was triturated with ethyl acetate overnight, collected by filtration, and dried to give 4-chloro-2-[2-ethoxy-4-(methylaminomethyl)phenoxy]benzonitrile fumarate (707 mg, 74%) as a white solid.

MS (APCI+) 317/319[M+1]+.

$^1$H-NMR (300 MHz, $d_6$-DMSO): □ 7.92 (1H, d), 7.38 (1H, br s), 7.34-7.27 (2H, m), 7.10 (1H, br d), 6.67 (1H, br s), 6.49 (2H, s), 4.04 (2H, q), 3.97(2H, s), 2.46 (3H, s), 1.12 (3H, t).

EXAMPLE 24

4-Chloro-2-[4-(methylaminomethyl)naphthalen-1-yloxy]benzonitrile fumarate a) 4-Chloro-2-(4-formylnaphthalen-1-yloxy)benzonitrile 4-Chloro-2-fluorobenzonitrile (0.31 g, 2.0 mmol), 4-hydroxy-1-naphthaldehyde (0.34 g, 2.0 mmol) and cesium carbonate (0.64 g, 2.0 mmol) were heated with stirring in dry DMF (4 mL) at ambient temperature for 10 days. The reaction mixture was poured into water and extracted with ethyl acetate. The ethyl acetate layer was separated, washed with 1N sodium hydroxide solution (2×), water (1×), brine (1×), and dried over MgSO$_4$. After filtration, the solvent was removed in vacuo to yield 4-chloro-2-(4-formylnaphthalen-1-yloxy)benzonitrile (0.34 g, 56%) as a tan solid, which was used without further purification.

$^1$H-NMR (300 MHz, CDCl$_3$): δ 10.36 (1H, s), 9.35 (1H, d), 8.27 (1H, br d), 7.99 (1H, d), 7.83-7.77 (1H, m), 7.73-7.63 (2H, m), 7.29 (1H, br d), 7.09 (1H, d), 6.98 (1H, d).

b) 4-Chloro-2-[4-(methylaminomethyl)naphthalen-1-yloxy]benzonitrile fumarate

4-Chloro-2-(4-formylnaphthalen-1-yloxy)benzonitrile (0.34 g, 1.1 mmol), methylamine (2M in methanol, 2.0 mL, 4.0 mmol) and sodium cyanoborohydride (80 mg, 1.3 mmol) were stirred at ambient temperature in a 1% acetic acid/methanol solution (30 mL) for 18 h. The solvent was removed in vacuo. The residue was treated with 10% sodium carbonate solution and extracted with ethyl acetate. The ethyl acetate layer was separated and fumaric acid (0.12 g, 1.0 mmol) was added. After the solvent was removed in vacuo, the residue was triturated with ethyl acetate overnight, collected by filtration, and dried to give 4-chloro-2-[4-(methylaminomethyl)naphthalen-1-yloxy]benzonitrile fumarate (328 mg, 68%) as an off-white solid.

MS (APCI+) 323/325 [M+1]+. $^1$H-NMR (300 MHz, $d_6$-DMSO): δ 8.32 (1H, d), 8.05-7.98 (2H, m), 7.74-7.60 (3H, m), 7.41 (1H, dd), 7.30 (1H, d), 6.86 (1H, br d), 6.49 (2H, s), 4.33 (2H, s), 2.50 (3H, s).

EXAMPLE 25

4-Chloro-2-[3-(dimethylaminomethyl)phenoxy]benzonitrile fumarate

4-Chloro-2-(3-formylphenoxy)benzonitrile (0.20 g, 0.78 mmol), dimethylamine (2M in methanol, 1.0 mL, 2.0 mmol) and sodium cyanoborohydride (60 mg, 0.96 mmol) were stirred at ambient temperature in a 1% acetic acid/methanol solution (20 mL) for 18 h. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-[3-(dimethylaminomethyl)phenoxy]benzonitrile fumarate (179 mg, 58%) as a white solid.

MS (APCI+) 287/289 [M+1]+.

$^1$H-NMR (300 MHz, $d_6$-DMSO): δ 7.96 (1H, d), 7.48 (1H, br t), 7.39 (1H, dd), 7.30 (1H, br d), 7.22-7.12 (2H, m), 6.99 (1H, d), 6.60 (2H, s), 3.64 (2H, s), 2.28 (6H, s).

EXAMPLE 26

4-Chloro-2-{3-[(2-(hydroxyethyl)amino)methyl]phenoxy}benzonitrile fumarate

4-Chloro-2-(3-formylphenoxy)benzonitrile (0.20 g, 0.78 mmol), ethanolamine (50 μL, 51 mg, 0.83 mmol) and sodium cyanoborohydride (60 mg, 0.96 mmol) were stirred at ambient temperature in a 1% acetic acid/methanol solution (20 mL) for 40 h. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-{3-[(2-(hydroxyethyl)amino)methyl]phenoxy}benzonitrile fumarate (240 mg, 73%) as a white solid.

MS (APCI+) 303/305 [M+1]$^+$.

$^1$H-NMR (300 MHz, d$_6$-DMSO): δ 7.97 (1H, d), 7.49 (1H, t), 7.41-7.35 (2H, m), 7.31 (1H, br s), 7.16 (1H, br d), 6.97 (1H, br s), 6.53 (2H, s), 3.97 (2H, s), 3.57 (2H, t), 2.77 (2H, t).

EXAMPLE 27

4-Chloro-2-{3-[(2-methoxyethylamino)methyl]phenoxy}benzonitrile fumarate

4-Chloro-2-(3-formylphenoxy)benzonitrile (0.20 g, 0.78 mmol), 2-methoxyethylamine (72 μL, 62 mg, 0.83 mmol) and sodium cyanoborohydride (60 mg, 0.96 mmol) were stirred at ambient temperature in a 1% acetic acid/methanol solution (20 mL) for 40 h. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-{3-[(2-methoxyethylamino)methyl]phenoxy}benzonitrile fumarate (208 mg, 61%) as a white solid.

MS (APCI+) 317/319 [M+1]$^+$.

$^1$H-NMR (300 MHz, d$_6$-DMSO): δ 7.96 (1H, d), 7.45 (1H, t), 7.39 (1H, dd), 7.30 (1H, br d), 7.22 (1H, br s), 7.11 (1H, br d), 6.94 (1H, br s), 6.62 (2H, s), 3.84 (2H, s), 3.43 (2H, t), 3.23 (3H, s), 2.73 (2H, t).

EXAMPLE 28

4-Chloro-2-[3-(propylaminomethyl)phenoxy]benzonitrile fumarate

4-Chloro-2-(3-formylphenoxy)benzonitrile (0.20 g, 0.78 mmol), n-propylamine (140 μL, 101 mg, 1.7 mmol) and sodium cyanoborohydride (60 mg, 0.96 mmol) were stirred at ambient temperature in a 1% acetic acid/methanol solution (20 mL) for 5 days. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-[3-(propylaminomethyl)phenoxy]benzonitrile fumarate (250 mg, 78%) as a white solid.

MS (APCI+) 301/303 [M+1]$^+$.

$^1$H-NMR (300 MHz, d$_6$-DMSO): δ 7.97 (1H, d), 7.49 (1H, t), 7.40 (1H, dd), 7.35 (1H, br d), 7.29 (1H, br s), 7.17 (1H, br dd), 6.96 (1H, br s), 6.46 (2H, s), 3.94 (2H, s), 2.63 (2H, t), 1.61-1.46 (2H, m), 0.86 (3H, t).

EXAMPLE 29

4-Chloro-2-{3-[(2-dimethylaminoethylamino)methyl]phenoxy}benzonitrile fumarate

4-Chloro-2-(3-formylphenoxy)benzonitrile (0.20 g, 0.78 mmol), N,N-dimethylethylenediamine (90 μL, 72 mg, 0.82 mmol) and sodium cyanoborohydride (60 mg, 0.96 mmol) were stirred at ambient temperature in a 1% acetic acid/methanol solution (20 mL) for 5 days. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-{3-[(2-dimethylaminoethylamino)methyl]phenoxy}benzonitrile fumarate (315 mg, 90%) as a white solid.

MS (APCI+) 330/332 [M+1]$^+$.

$^1$H-NMR (300 MHz, d$_6$-DMSO): δ 7.98 (1H, d), 7.47 (1H, t), 7.40 (1H, dd), 7.31 (1H, br d), 7.25 (1H, br s), 7.13 (1H, br dd), 6.94 (1H, br s), 6.49 (2H, s), 3.85 (2H, s), 2.71 (2H, t), 2.55 (2H, t), 2.26 (6H, s).

EXAMPLE 30

4-Chloro-2-{3-[(3-hydroxypropylamino)methyl]phenoxy}benzonitrile fumarate

4-Chloro-2-(3-formylphenoxy)benzonitrile (0.21 g, 0.81 mmol), 3-aminopropan-1-ol (65 μL, 64 mg, 0.85 mmol) and sodium cyanoborohydride (60 mg, 0.96 mmol) were stirred at ambient temperature in a 1% acetic acid/methanol solution (20 mL) for 5 days. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-{3-[(3-hydroxypropylamino)methyl]phenoxy}benzonitrile fumarate (352 mg, 99%) as a white solid.

MS (APCI+) 317/319 [M+1]$^+$.

$^1$H-NMR (300 MHz, d$_6$-DMSO): δ 7.97 (1H, d), 7.48 (1H, t), 7.39 (1H, dd), 7.35 (1H, br d), 7.29 (1H, br s), 7.16 (1H, br dd), 6.95 (1H, br s), 6.46 (2H, s), 3.93 (2H, s), 3.45 (2H, t), 2.72 (2H, t), 1.71-1.61 (2H, m).

EXAMPLE 31

4-Chloro-2-[3-(pyrrolidin-1-ylmethyl)phenoxy]benzonitrile fumarate

4-Chloro-2-(3-formylphenoxy)benzonitrile (0.20 g, 0.78 mmol), pyrrolidine (0.14 mL, 0.12 g, 1.7 mmol) and sodium cyanoborohydride (60 mg, 0.96 mmol) were stirred at ambient temperature in a 1% acetic acid/methanol solution (20 mL) for 5 days. The solvent was removed in vacuo. The residue was treated with 10% sodium carbonate solution and extracted with ethyl acetate. The ethyl acetate layer was separated and fumaric acid (0.10 g, 0.86 mmol) was added. After the solvent was removed in vacuo, the residue was triturated with ethyl acetate overnight, collected by filtration, and dried to give 4-chloro-2-[3-(pyrrolidin-1-ylmethyl)phenoxy]benzonitrile fumarate (117 mg, 35%) as a white solid.

MS (APCI+) 313/315 [M+1]$^+$.

$^1$H-NMR (300 MHz, d$_6$-DMSO): δ 7.97 (1H, d), 7.45 (1H, t), 7.39 (1H, dd), 7.27 (1H, br d), 7.17 (1H, br s), 7.11 (1H, br d), 6.95 (1H, br s), 6.48 (2H, s), 3.68 (2H, s), 3.11-3.05 (4H, m), 1.85-1.77 (2H, m), 1.75-1.67 (2H, m).

EXAMPLE 32

4-Chloro-5-fluoro-2-(2-methoxy-3-methylaminomethylphenoxy)benzonitrile fumarate a) 4-Chloro-2,5-difluorobenzamide 4-Chloro-2,5-difluorobenzoic acid (2.05 g, 10.6 mmol) was suspended in dry toluene (40 mL, plus two drops DMF)

with cooling in an ice water bath. Oxalyl chloride (2.4 mL, 3.5 g, 27.5 mmol) was added and reaction mixture was allowed to reach ambient temperature with stirring. After 18 h, the solvent was removed in vacuo and the residue dissolved in 2-methoxyethyl ether (6 mL), which was added to concentrated ammonium hydroxide (80 mL) with stirring. After 1 h, the resulting precipitate was collected by filtration, washed with water and dried to give 4-chloro-2,5-difluorobenzamide (1.52 g, 75%) as a beige solid.

MS (APCI+) 192 [M+1]+.

$^1$H-NMR (300 MHz, CDCl$_3$): δ 7.96-7.88 (1H, m), 7.30-7.22 (1H, m), 6.61 (1H, br s), 5.98 (1H, br s).

b) 4-Chloro-2,5-difluorobenzonitrile

4-Chloro-2,5-difluorobenzamide (1.50 g, 7.83 mmol) was dissolved in dry DMF (10 mL) and cooled with an ice-water bath. Thionyl chloride (2.8 mL, 4.6 g, 38 mmol) was added, and the resulting solution was heated to 80° C. with stirring for 2.5 h. The cooled reaction mixture was poured into water and extracted with ethyl acetate. The ethyl acetate layer was washed with water (1×), saturated sodium hydrogen carbonate (1×), water (3×), brine (1×), and dried over MgSO$_4$. After filtration, the solvent was removed in vacuo to give a yellowish tan solid (0.60 g). Purification by chromatography gave 4-chloro-2,5-difluorobenzonitrile (0.48 g, 35%) as a tan crystalline solid.

$^1$H-NMR (300 MHz, CDCl$_3$): δ 7.42 (1H, dd), 7.35 (1H, dd).

c) 4-Chloro-5-fluoro-2-(3-formyl-2-methoxyphenoxy)benzonitrile

4-Chloro-2,5-difluorobenzonitrile (0.45 g, 2.6 mmol), 3-hydroxy-2-methoxybenzaldehyde (0.39 g, 2.6 mmol) and cesium carbonate (0.84 g, 2.6 mmol) were heated with stirring in dry DMF (5 mL) at 50° C. for 18 h. The reaction mixture was cooled, poured into 0.1N sodium hydroxide solution and extracted with ethyl acetate. The ethyl acetate layer was separated, washed with 0.1N sodium hydroxide solution (1×), water (2×), brine (1×), and dried over MgSO$_4$. After filtration, the solvent was removed in vacuo, and purified by chromatography to yield 4-chloro-5-fluoro-2-(3-formyl-2-methoxyphenoxy)benzonitrile (0.33 g, 42%) as a pale yellow solid.

$^1$H-NMR (300 MHz, CDCl$_3$): δ 10.40 (1H, s), 7.81 (1H, dd), 7.47 (1H, d), 7.38 (1H, dd), 7.30 (1H, d), 6.76 (1H, d), 4.01 (3H, s).

d) 4-Chloro-5-fluoro-2-(2-methoxy-3-methylaminomethylphenoxy)benzonitrile fumarate 4-Chloro-5-fluoro-2-(3-formyl-2-methoxyphenoxy)benzonitrile (0.29 g, 0.95 mmol), methylamine (33% in ethanol, 1.0 mL, 8.0 mmol) and sodium cyanoborohydride (90 mg, 1.4 mmol) were stirred at ambient temperature in a 1% acetic acid/methanol solution (50 mL) for 44 h. The solvent was removed in vacuo. The residue was treated with 10% sodium carbonate solution and extracted with ethyl acetate. The ethyl acetate layer was separated and fumaric acid (65 mg, 0.56 mmol) was added. After the solvent was removed in vacuo, the residue was triturated with ethyl acetate overnight, collected by filtration, and dried to give 4-chloro-5-fluoro-2-(2-methoxy-3-methylaminomethylphenoxy)benzonitrile fumarate (143 mg, 35%) as a white solid.

MS (APCI+) 321/323 [M+1]+.

$^1$H-NMR (300 MHz, d$_6$-DMSO): δ 8.20 (1H, d), 7.42-7.38 (1H, m), 7.25-7.17 (2H, m), 7.03 (1H, d), 6.48 (2H, s), 3.89 (2H, s), 3.79 (3H, s), 2.42 (3H, s).

EXAMPLE 33

4-Bromo-2-(2-methoxy-3-methylaminomethyl-phenoxy)-benzonitrile fumarate a)
4-Bromo-2-(3-formyl-2-methoxyphenoxy)benzonitrile 4-Bromo-2-fluorobenzonitrile (0.41 g, 2.0 mmol), 3-hydroxy-2-methoxybenzaldehyde (0.31 g, 2.0 mmol) and cesium carbonate (0.66 g, 2.0 mmol) were heated with stirring in dry DMF (4 mL) at 50° C. for 18 h. The reaction mixture was cooled, poured into water and extracted with ethyl acetate. The ethyl acetate layer was separated, washed with 1N sodium hydroxide solution (2×), water (1×), brine (1×), and dried over MgSO$_4$. After filtration, the solvent was removed in vacuo to yield 4-bromo-2-(3-formyl-2-methoxyphenoxy)-benzonitrile (0.55 g, 81%) as a yellow solid.

MS (APCI+) 332/334 [M+1]+.

$^1$H-NMR (300 MHz, CDCl$_3$): δ 10.41 (1H, s), 7.81 (1H, dd), 7.54 (1H, d), 7.40 (1H, dd), 7.34-7.28 (2H, m), 6.85 (1H, d), 4.01 (3H, s).

b) 4-Bromo-2-(2-methoxy-3-methylaminomethyl-phenoxy)-benzonitrile fumarate

4-Bromo-2-(3-formyl-2-methoxyphenoxy)benzonitrile (0.55 g, 1.7 mmol), methylamine (2M in methanol, 3.0 mL, 6.0 mmol) and sodium cyanoborohydride (120 mg, 1.9 mmol) were stirred at ambient temperature in a 1% acetic acid/methanol solution (40 mL) for 17 h. The solvent was removed in vacuo. The residue was treated with 10% sodium carbonate solution and extracted with ethyl acetate. The ethyl acetate layer was separated and fumaric acid (0.20 g, 1.7 mmol) was added. After the solvent was removed in vacuo, the residue was triturated with ethyl acetate overnight, collected by filtration, and dried to give 4-bromo-2-(2-methoxy-3-methylaminomethyl-phenoxy)-benzonitrile fumarate (546 mg, 71%) as a white solid.

MS (APCI+) 347/349 [M+1]+.

$^1$H-NMR (300 MHz, d$_6$-DMSO): δ 7.88 (1H, d), 7.50 (1H, dd), 7.46-7.41 (1H, m), 7.28-7.22 (2H, m), 6.89 (1H, d), 6.49 (2H, s), 3.94 (2H, s), 3.79 (3H, s), 2.44 (3H, s).

EXAMPLE 34

2-(2-Methoxy-3-methylaminomethyl-phenoxy)-6-trifluoromethyl-nicotinonitrile fumarate a) 2-(3-Formyl-2-methoxyphenoxy)-6-(trifluoromethyl)nicotinonitrile 2-Chloro-6-(trifluoromethyl)nicotinonitrile (0.34 g, 1.6 mmol), 3-hydroxy-2-methoxybenzaldehyde (0.25 g, 1.6 mmol) and potassium fluoride (0.29 g, 4.9 mmol) were heated with stirring in dry DMF (4 mL) at 120° C. for 3 h. The reaction mixture was cooled, poured into 1N sodium hydroxide solution and extracted with ethyl acetate. The ethyl acetate layer was separated, washed with 1N sodium hydroxide solution (3×), water (3×), brine (1×), and dried over MgSO$_4$. After filtration, the solvent was removed in vacuo to yield 2-(3-formyl-2-methoxyphenoxy)-6-(trifluoromethyl)nicotinonitrile (0.50 g, 94%) as a yellow solid.

MS (APCI+) 323 [M+1]$^+$.

$^1$H-NMR (300 MHz, CDCl$_3$): δ 10.37 (1H, s), 8.23 (1H, d), 7.81 (1H, dd), 7.54-7.47 (2H, m), 7.32-7.26 (1H, m), 3.96 (3H, s).

b) 2-(2-Methoxy-3-methylaminomethyl-phenoxy)-6-trifluoromethyl-nicotinonitrile fumarate 2-(3-Formyl-2-methoxyphenoxy)-6-(trifluoromethyl) nicotinonitrile (0.50 g, 1.6 mmol), methylamine (33% in ethanol, 0.9 mL, 7.2 mmol) and sodium cyanoborohydride (120 mg, 1.9 mmol) were stirred at ambient temperature in a 1% acetic acid/methanol solution (80 mL) for 18 h. The solvent was removed in vacuo. The residue was treated with 10% sodium carbonate solution and extracted with ethyl acetate. The ethyl acetate layer was separated and fumaric acid (0.20 g, 1.7 mmol) was added. After the solvent was removed in vacuo, the residue was triturated with ethyl acetate overnight, collected by filtration, and dried to give 2-(2-methoxy-3-methylaminomethyl-phenoxy)-6-trifluoromethyl-nicotinonitrile fumarate (468 mg, 67%) as a white solid.

MS (APCI+) 338 [M+1]$^+$.

$^1$H-NMR (300 MHz, d$_6$-DMSO): δ 8.78 (1H, d), 7.85 (1H, d), 7.48 (1H, d), 7.37 (1H, d), 7.28-7.22 (1H, m), 6.50 (2H, s), 3.97 (2H, s), 3.74 (3H, s), 2.40 (3H, s).

EXAMPLE 35

4-Methoxy-2-(2-methoxy-3-methylaminomethyl-phenoxy)-benzonitrile fumarate a) 2-Fluoro-4-methoxy-benzonitrile 2-Fluoro-4-hydroxybenzonitrile (0.50 g, 3.7 mmol), potassium carbonate (0.53 g, 3.8 mmol) and iodomethane (0.34 mL, 0.78 g, 5.5 mmol) in dry DMF (5 mL) were stirred at ambient temperature for 21 h. The reaction mixture was poured into water and extracted with ethyl acetate. The ethyl acetate layer was washed with 1N sodium hydroxide solution (2×), water (3×), brine (1×), and dried over MgSO$_4$. After filtration, the solvent was removed in vacuo to yield 2-fluoro-4-methoxy-benzonitrile (0.54 g, 98%) as a white crystalline solid.

$^1$H-NMR (300 MHz, CDCl$_3$): δ 7.55-7.48 (1H, m), 6.77 (1H, dd), 6.71 (1H, dd), 3.86 (3H, s).

b) 2-(3-Formyl-2-methoxy-phenoxy)-4-methoxy-benzonitrile

2-Fluoro-4-methoxy-benzonitrile (0.28 g, 1.8 mmol), 3-hydroxy-2-methoxybenzaldehyde (0.28 g, 1.8 mmol) and cesium carbonate (0.90 g, 2.4 mmol) were heated with stirring in dry DMF (4 mL) at 50° C. for 40 h. The reaction mixture was cooled, poured into 1N sodium hydroxide solution and extracted with ethyl acetate. The ethyl acetate layer was separated, washed with 1N sodium hydroxide solution (4×), water (4×), brine (1×), and dried over MgSO$_4$. After filtration, the solvent was removed in vacuo to yield 2-(3-formyl-2-methoxy-phenoxy)-4-methoxy-benzonitrile (0.38 g, 73%) as a tan oil.

MS (APCI+) 284 [M+1]$^+$.

$^1$H-NMR (300 MHz, d$_6$-DMSO): δ 10.42 (1H, s), 7.75 (1H, dd), 7.60 (1H, br d), 7.36 (1H, dd), 7.27-7.21 (1H, m), 6.68 (1H, br dd), 6.21 (1H, br d), 4.04 (3H, s), 3.75 (3H, s).

c) 4-Methoxy-2-(2-methoxy-3-methylaminomethyl-phenoxy)-benzonitrile fumarate 2-(3-Formyl-2-methoxy-phenoxy)-4-methoxy-benzonitrile (0.38 g, 1.3 mmol), methylamine (2M in methanol, 3.0 mL, 6.0 mmol) and sodium cyanoborohydride (110 mg, 1.8 mmol) were stirred at ambient temperature in a 1% acetic acid/methanol solution (50 mL) for 17 h. The solvent was removed in vacuo. The residue was treated with 10% sodium carbonate solution and extracted with ethyl acetate. The ethyl acetate layer was to separated and fumaric acid (0.15 g, 1.3 mmol) was added. After the solvent was removed in vacuo, the residue was triturated with ethyl acetate overnight, collected by filtration, and dried to give 4-methoxy-2-(2-methoxy-3-methylaminomethyl-phenoxy)-benzonitrile fumarate (326 mg, 58%) as an off-white solid.

MS (APCI+) 299 [M+1]$^+$.

$^1$H-NMR (300 MHz, d$_6$-DMSO): δ 7.83 (1H, d), 7.39 (1H, br d), 7.24-7.14 (2H, m), 6.85 (1H, dd), 6.48 (2H, s), 6.21 (1H, d), 3.93 (2H, s), 3.80 (3H, s), 3.73 (3H, s), 2.43 (3H, s).

EXAMPLE 36

3-Fluoro-2-(2-methoxy-3-(methylaminomethyl)phenoxy)-4-methyl-benzonitrile fumarate a) 2,3-Difluoro-4-methylbenzonitrile 2,3-Difluoro-4-methylbenzamide (1.02 g, 5.96 mmol) was dissolved in dry DMF (8 mL) and cooled with an ice-water bath. Thionyl chloride (2.2 mL, 3.6 g, 30 mmol) was added, and the resulting solution was heated to 80° C. with stirring for 8 h. The cooled reaction mixture was poured into water and extracted with diethyl ether. The ether layer was washed with water (1×), saturated sodium hydrogen carbonate (1×), water (1×), brine (1×), and dried over MgSO$_4$. After filtration, the solvent was removed in vacuo to give a dark orange solid (0.87 g). Purification by chromatography gave 2,3-difluoro-4-methylbenzonitrile (0.28 g, 30%) as a yellow solid.

$^1$H-NMR (300 MHz, CDCl$_3$): δ 7.32-7.25 (1H, m), 7.10-7.03 (1H, m), 2.39 (3H, d).

b) 3-Fluoro-2-(3-formyl-2-methoxyphenoxy)-4-methylbenzonitrile 2,3-Difluoro-4-methylbenzonitrile (0.21 g, 1.4 mmol), 3-hydroxy-2-methoxybenzaldehyde (0.21 g, 1.4 mmol) and cesium carbonate (0.45 g, 1.4 mmol) were heated with stirring in dry DMF (4 mL) at 50° C. for 18 h. The reaction mixture was cooled, poured into 0.1N sodium hydroxide solution and extracted with diethyl ether. The ether layer was separated, washed with 0.1N sodium hydroxide solution (2×), water (3×), brine (1×), and dried over MgSO$_4$. After filtration, the solvent was removed in vacuo, and purified by chromatography to yield 3-fluoro-2-(3-formyl-2-methoxyphenoxy)-4-methylbenzonitrile (0.12 g, 31%) as a colourless glass.

MS (APCI+) 286 [M+1]$^+$.

$^1$H-NMR (300 MHz, CDCl$_3$): δ 10.45 (1H, s), 7.61 (1H, br d), 7.40 (1H, br d), 7.19-7.06 (2H, m), 6.95 (1H, br d), 4.12 (3H, s), 2.37 (3H, d).

c) 3-Fluoro-2-(2-methoxy-3-(methylaminomethyl) phenoxy)-4-methyl-benzonitrile fumarate 3-Fluoro-2-(3-formyl-2-methoxyphenoxy)-4-methylbenzonitrile (0.10 g, 0.35 mmol), methylamine (33% in ethanol; 0.5 mL, 4.0 mmol) and sodium cyanoborohydride (30 mg, 0.48 mmol) were stirred at ambient temperature in a 1% acetic acid/methanol solution (25 mL) for 67 h. The solvent was removed in vacuo. The residue was treated with 10% sodium carbonate solution and extracted with ethyl acetate. The ethyl acetate layer was separated and fumaric acid (41 mg, 0.35 mmol) was added. After the solvent was removed in vacuo, the residue was triturated with ethyl acetate overnight, collected by filtration, and dried to give 3-fluoro-2-(2-methoxy-3-(methylaminomethyl)phenoxy)-4-methyl-benzonitrile fumarate (83 mg, 57%) as a white solid.

MS (APCI+) 301 [M+1]$^+$.

$^1$H-NMR (300 MHz, d$_6$-DMSO): δ 7.72 (1H, d), 7.43 (1H, t), 7.26 (1H, d), 7.13 (1H, t), 6.82 (1H, d), 6.66 (2H, s), 4.23 (2H, s), 4.00 (3H, s), 2.64 (3H, s), 2.38 (3H, s).

EXAMPLE 37

2-(2-Methoxy-3-methylaminomethyl-phenoxy)-6-methyl-nicotinonitrile fumarate a) 2-(3-Formyl-2-methoxy-phenoxy)-6-methyl-nicotinonitrile

2-Chloro-6-methylnicotinonitrile (0.25 g, 1.6 mmol), 3-hydroxy-2-methoxybenzaldehyde (0.25 g, 1.6 mmol) and potassium fluoride (0.29 g, 4.9 mmol) were heated with stirring in dry DMF (4 mL) at 120° C. for 5 h. The reaction mixture was cooled, poured into 1N sodium hydroxide solution and extracted with ethyl acetate. The ethyl acetate layer was separated, washed with 1N sodium hydroxide solution (2×), water (3×), brine (1×), and dried over MgSO$_4$. After filtration, the solvent was removed in vacuo to yield 2-(3-formyl-2-methoxy-phenoxy)-6-methyl-nicotinonitrile (0.30 g, 68%) as a yellow solid.

MS (APCI+) 269 [M+1]$^+$.

$^1$H-NMR (300 MHz, CDCl$_3$): δ 10.39 (1H, s), 7.89 (1H, d), 7.76 (1H, dd), 7.46 (1H, dd), 7.28-7.20 (1H, m), 6.97 (1H, d), 3.97 (3H, s), 2.38 (3H, s).

b) 2-(2-Methoxy-3-methylaminomethyl-phenoxy)-6-methyl-nicotinonitrile fumarate 2-(3-Formyl-2-methoxy-phenoxy)-6-methyl-nicotinonitrile (0.30 g, 1.1 mmol), methylamine (2M in methanol, 3.0 mL, 6.0 mmol) and sodium cyanoborohydride (90 mg, 1.4 mmol) were stirred at ambient temperature in a 1% acetic acid/methanol solution (50 mL) for 20 h. The solvent was removed in vacuo. The residue was treated with 10% sodium carbonate solution and extracted with ethyl acetate. The ethyl acetate layer was separated and fumaric acid (0.13 g, 1.1 mmol) was added. After the solvent was removed in vacuo, the residue was triturated with ethyl acetate overnight, collected by filtration, and dried to give 2-(2-methoxy-3-methylaminomethyl-phenoxy)-6-methyl-nicotinonitrile fumarate (180 mg, 40%) as an off-white solid.

MS (APCI+) 284 [M+1]$^+$.

$^1$H-NMR (300 MHz, d$_6$-DMSO): δ 8.28 (1H, d), 7.36 (1H, dd), 7.26-7.15 (3H, m), 6.48 (2H, s), 3.88 (2H, s), 3.72 (3H, s), 2.40 (3H, s), 2.32 (3H, s).

EXAMPLE 38

6-Ethyl-2-(2-methoxy-3-methylaminomethyl-phenoxy)-nicotinonitrile difumarate a) 6-Ethyl-2-(3-formyl-2-methoxy-phenoxy)-nicotinonitrile

2-Chloro-6-ethylnicotinonitrile (0.27 g, 1.6 mmol), 3-hydroxy-2-methoxybenzaldehyde (0.25 g, 1.6 mmol) and potassium fluoride (0.29 g, 4.9 mmol) were heated with stirring in dry DMF (4 mL) at 120° C. for 6 h, then at 80° C. for 16 h. The reaction mixture was cooled, poured into 1N sodium hydroxide solution and extracted with ethyl acetate. The ethyl acetate layer was separated, washed with 1N sodium hydroxide solution (3×), water (4×), brine (1×), and dried over MgSO$_4$. After filtration, the solvent was removed in vacuo to yield 6-ethyl-2-(3-formyl-2-methoxy-phenoxy)-nicotinonitrile (0.28 g, 61%) as a yellow oil.

MS (APCI+) 283 [M+1]$^+$.

$^1$H-NMR (300 MHz, CDCl$_3$): δ 10.40 (1H, s), 7.91 (1H, d), 7.76 (1H, dd), 7.46 (1H, dd), 7.27-7.20 (1H, m), 6.97 (1H, d), 3.98 (3H, s), 2.65 (2H, q), 1.10 (3H, t).

b) 6-Ethyl-2-(2-methoxy-3-methylaminomethyl-phenoxy)-nicotinonitrile difumarate 6-Ethyl-2-(3-formyl-2-methoxy-phenoxy)-nicotinonitrile (0.28 g, 1.0 mmol), methylamine (33% in ethanol, 0.8 mL, 6.4 mmol) and sodium cyanoborohydride (80 mg, 1.3 mmol) were stirred at ambient temperature in a 1% acetic acid/methanol solution (60 mL) for 16 h. The solvent was removed in vacuo. The residue was treated with 10% sodium carbonate solution and extracted with ethyl acetate. The ethyl acetate layer was separated and fumaric acid (0.12 g, 1.0 mmol) was added. After the solvent was removed in vacuo, the residue was triturated with ethyl acetate overnight, collected by filtration, and dried to give 6-ethyl-2-(2-methoxy-3-methylaminomethyl-phenoxy)-nicotinonitrile difumarate (166 mg, 32%) as a beige solid.

MS (APCI+) 298 [M+1]$^+$.

$^1$H-NMR (300 MHz, d$_6$-DMSO): δ 8.30 (1H, d), 7.36 (1H, br d), 7.26-7.15 (3H, m), 6.47 (4H, s), 3.87 (2H, s), 3.71 (3H, s), 2.59 (2H, q), 2.38 (3H, s), 1.02 (3H, t).

EXAMPLE 39

4-Methyl-2-(3-methylaminomethyl-phenoxy)-benzonitrile fumarate a) 2-(3-Formyl-phenoxy)-4-methyl-benzonitrile

4-Methyl-2-nitrobenzonitrile (0.50 g, 3.1 mmol), 3-hydroxybenzaldehyde (0.38 g, 3.1 mmol) and cesium carbonate (1.00 g, 3.1 mmol) were heated with stirring in dry DMF (5 mL) at 80° C. for 28 h. The reaction mixture was cooled, poured into water and extracted with ethyl acetate. The ethyl acetate layer was separated, washed with 0.1N sodium hydroxide solution (3×), water (1×), brine (1×), and dried over MgSO$_4$. After filtration, the solvent was removed in vacuo to yield 2-(3-formyl-phenoxy)-4-methyl-benzonitrile (0.26 g, 36%) as a brown resin, and was carried forward without further purification.

MS (APCI+) 233 [M+1]$^+$.

$^1$H-NMR (300 MHz, CDCl$_3$): δ 10.00 (1H, s), 7.71 (1H, br d), 7.62-7.55 (2H, m), 7.53-7.49 (1H, m), 7.36 (1H, br dd), 7.03 (1H, br d), 6.74 (1H, br s), 2.35 (3H, s).

b) 4-Methyl-2-(3-methylaminomethyl-phenoxy)-benzonitrile fumarate 2-(3-Formyl-phenoxy)-4-methyl-benzonitrile (0.26 g, 1.1 mmol), methylamine (2M in methanol, 2.5 mL, 5.0 mmol) and sodium cyanoborohydride (80 mg, 1.3 mmol) were stirred at ambient temperature in a 1% acetic acid/methanol solution (30 mL) for 18 h. The solvent was removed in vacuo. The residue was treated with 10% sodium carbonate solution and extracted with ethyl acetate. The ethyl acetate layer was separated and fumaric acid (0.12 g, 1.1 mmol) was added. After the solvent was removed in vacuo, the residue was triturated with ethyl acetate overnight, collected by filtration, and dried to give 4-methyl-2-(3-methylaminomethyl-phenoxy)-benzonitrile fumarate (78 mg, 20%) as a tan solid.

MS (APCI+) 253 [M+1]$^+$.

$^1$H-NMR (300 MHz, d$_6$-DMSO): δ 7.89 (1H, d), 7.44 (1H, t), 7.30-7.03 (4H, m), 6.81 (1H, br s), 6.44 (2H, s), 3.86 (2H, s), 2.36 (3H, s), 2.31 (3H, s).

EXAMPLE 40

6-Methyl-2-(3-methylaminomethyl-phenoxy)-nicotinonitrile fumarate a) 2-(3-Formyl-phenoxy)-6-methyl-nicotinonitrile

2-Chloro-6-methylnicotinonitrile (0.50 g, 3.3 mmol), 3-hydroxybenzaldehyde (0.40 g, 3.3 mmol) and potassium fluoride (0.57 g, 9.8 mmol) were heated with stirring in dry DMF (5 mL) at 120° C. for 7 h. The reaction mixture was cooled, poured into water and extracted with ethyl acetate. The ethyl acetate layer was separated, washed with 1N sodium hydroxide solution (4×), water (4×), brine (1×), and dried over MgSO$_4$. After filtration, the solvent was removed in vacuo to yield 2-(3-formyl-phenoxy)-6-methyl-nicotinonitrile (0.77 g, 97%) as a yellow solid.

MS (APCI+) 239 [M+1]$^+$.

$^1$H-NMR (300 MHz, CDCl$_3$): δ 10.03 (1H, s), 7.89 (1H, d), 7.77 (1H, br d), 7.72 (1H, br d), 7.59 (1H, dd), 7.47 (1H, br d), 6.98 (1H, d), 2.41 (3H, s).

b) 6-Methyl-2-(3-methylaminomethyl-phenoxy)-nicotinonitrile fumarate 2-(3-Formyl-phenoxy)-6-methyl-nicotinonitrile (0.77 g, 3.2 mmol), methylamine (2M in methanol, 7.0 mL, 14 mmol) and sodium cyanoborohydride (250 mg, 4.0 mmol) were s stirred at ambient temperature in a 1% acetic acid/methanol solution (100 mL) for 20 h. The solvent was removed in vacuo. The residue was treated with 10% sodium carbonate solution and extracted with ethyl acetate. The ethyl acetate layer was separated and fumaric acid (0.36 g, 3.1 mmol) was added. After the solvent was removed in vacuo, the residue was triturated with ethyl acetate overnight, collected by filtration, and dried to give 6-methyl-2-(3-methylaminomethyl-phenoxy)-nicotinonitrile fumarate (650 mg, 55%) as an off-white solid.

MS (APCI+) 255 [M+1]$^+$.

$^1$H-NMR (300 MHz, d$_6$-DMSO): δ 8.27 (1H, d), 7.44 (1H, br t), 7.30 (1H, br s), 7.19 (1H, br d), 6.47 (2H, s), 3.92 (2H, s), 2.40 (3H, s), 2.35 (3H, s).

EXAMPLE 41

4-Chloro-2-(5-methylamino-5,6,7,8-tetrahydronaphthalen-1-yloxy)-benzonitrile fumarate a) 4-Chloro-2-(5-oxo-5,6,7,8-tetrahydronaphthalen-1-yloxy)benzonitrile

4-Chloro-2-fluorobenzonitrile (0.30 g, 1.9 mmol), 5-hydroxy-3,4-dihydro-2H-naphthalen-1-one (0.31 g, 1.9 mmol) and cesium carbonate (0.63 g, 1.9 mmol) were heated with stirring in dry DMF (4 mL) at 50° C. for 18 h. The reaction mixture was cooled, poured into 0.1N sodium hydroxide solution and extracted with ethyl acetate. The ethyl acetate layer was separated, washed with 0.1N sodium hydroxide solution (1×), water (3×), brine (1×), and dried over MgSO$_4$. After filtration, the solvent was removed in vacuo to give an amber oil (0.61 g), which was purified by chromatography to yield 4-chloro-2-(5-oxo-5,6,7,8-tetrahydronaphthalen-1-yloxy)benzonitrile (0.22 g, 39%) as a white solid.

MS (APCI+) 298/300 [M+1]$^+$.

$^1$H-NMR (300 MHz, CDCl$_3$): δ 8.01 (1H, d), 7.62 (1H, d), 7.40 (1H, dd), 7.23 (1H, br d), 7.14 (1H, dd), 6.69 (1H, br d), 2.87 (2H, t), 2.68 (2H, t), 2.19-2.09 (2H, m).

b) 4-Chloro-2-(5-methylamino-5,6,7,8-tetrahydronaphthalen-1-yloxy)-benzonitrile fumarate 4-Chloro-2-(5-oxo-5,6,7,8-tetrahydronaphthalen-1-yloxy)benzonitrile (0.22 g, 0.74 mmol), methylamine (33% in ethanol, 0.7 mL, 5.6 mmol) and sodium cyanoborohydride (60 mg, 0.81 mmol) were stirred at ambient temperature in a 1% acetic acid/methanol solution (40 mL) for 6 days. The solvent was removed in vacuo. The residue was treated with 10% sodium carbonate solution and extracted with ethyl acetate. The ethyl acetate layer was separated and fumaric acid (70 mg, 0.60 mmol) was added. After the solvent was removed in vacuo, the residue was triturated with ethyl acetate overnight, collected by filtration, and dried to give 4-chloro-2-(5-methylamino-5,6,7,8-tetrahydronaphthalen-1-yloxy)benzonitrile fumarate (134 mg, 42%) as a white solid.

MS (APCI+) 313/315 [M+1]$^+$.

$^1$H-NMR (300 MHz, d$_6$-DMSO/d-TFA): δ 7.97 (1H, d), 7.49 (1H, d), 7.45-7.35 (2H, m), 7.21 (1H, d), 6.80 (2H, br d), 6.65 (2H, s), 4.53-4.47 (1H, m), 2.66 (3H, s), 2.75-2.55 (2H, m), 2.42-2.35 (2H, m), 2.15-1.95 (2H, m).

EXAMPLE 42

4-Chloro-2-(1-methylaminoindan-4-yloxy)benzonitrile fumarate a) 4-Chloro-2-(1-oxoindan-4-yloxy)benzonitrile

4-Chloro-2-fluorobenzonitrile (0.30 g, 1.9 mmol), 4-hydroxyindan-1-one (0.29 g, 1.9 mmol) and cesium carbonate (0.63 g, 1.9 mmol) were heated with stirring in dry DMF (4 mL) at 50° C. for 18 h. The reaction mixture was cooled, poured into 0.1N sodium hydroxide solution and extracted with ethyl acetate. The ethyl acetate layer was separated, washed with 0.1N sodium hydroxide solution (1×), water (3×), brine (1×), and dried over MgSO$_4$. After filtration, the solvent was removed in vacuo to give a brown oil (0.27 g), which was purified by chromatography to yield 4-chloro-2-(1-oxoindan-4-yloxy)benzonitrile (0.15 g, 27%) as a white solid.

MS (APCI+) 284/286 [M+1]+.

$^1$H-NMR (300 MHz, CDCl$_3$): δ 7.70 (1H, d), 7.63 (1H, d), 7.47 (1H, dd), 7.27 (1H, d), 7.18 (1H, dd), 6.81 (1H, d), 3.08-3.01 (2H, m), 2.76-2.70 (2H, m).

b) 4-Chloro-2-(1-methylaminoindan-4-yloxy)benzonitrile fumarate

4-Chloro-2-(1-oxoindan-4-yloxy)benzonitrile (0.12 g, 0.42 mmol), methylamine (33% in ethanol, 1.0 mL, 8.0 mmol) and sodium cyanoborohydride (100 mg, 0.86 mmol) were stirred at ambient temperature in a solution of glacial acetic acid (1.0 mL) in methanol (30 mL) for 5 days. The solvent was removed in vacuo. The residue was treated with 10% sodium carbonate solution and extracted with ethyl acetate. The ethyl acetate layer was separated and fumaric acid (40 mg, 0.34 mmol) was added. After the solvent was removed in vacuo, the residue was triturated with ethyl acetate overnight, collected by filtration, and dried to give 4-chloro-2-(1-methylaminoindan-4-yloxy)benzonitrile fumarate (111 mg, 63%) as a white solid.

MS (APCI+) 299/301 [M+1]+.

$^1$H-NMR (300 MHz, d$_6$-DMSO/d-TFA): δ 7.97 (1H, d), 7.56 (1H, d), 7.46 (1H, dd), 7.40 (1H, dd), 7.22 (1H, d), 6.89 (1H, br d), 6.65 (2H, s), 4.87-4.78 (1H, m), 3.03-2.89 (1H, m), 2.84-2.72 (1H, m), 2.64 (3H, s), 2.57-2.43 (1H, m), 2.27-2.13 (1H, m).

EXAMPLE 43

[2-Methoxy-3-(5-methyl-2-nitrophenoxy)benzyl]methylamine fumarate a) 2-Methoxy-3-(5-methyl-2-nitrophenoxy)benzaldehyde

2-Fluoro-4-methyl-1-nitrobenzene (0.25 g, 1.6 mmol), 3-hydroxy-2-methoxybenzaldehyde (0.25 g, 1.6 mmol) and cesium carbonate (0.54 g, 1.6 mmol) were heated with stirring in dry DMF (4 mL) at 50° C. for 20 h. The reaction mixture was cooled, poured into 0.1N sodium hydroxide solution and extracted with diethyl ether. The ether layer was separated, washed with 0.1N sodium hydroxide solution (4×), water (4×), brine (1×), and dried over MgSO$_4$. After filtration, the solvent was removed in vacuo to give 2-methoxy-3-(5-methyl-2-nitrophenoxy)benzaldehyde (0.36 g, 77%) as a brown oil, which was used without further purification.

$^1$H-NMR (300 MHz, CDCl$_3$): δ 10.43 (1H, s), 7.94 (1H, d), 7.71 (1H, dd), 7.24-6.95 (3H, m), 6.66 (1H, br s), 4.04 (3H, s), 2.34 (3H, s).

b) [2-Methoxy-3-(5-methyl-2-nitrophenoxy)benzyl]methylamine fumarate

2-Methoxy-3-(5-methyl-2-nitrophenoxy)benzaldehyde (0.36 g, 1.3 mmol), methylamine (2M in methanol, 3.0 mL, 6.0 mmol) and sodium cyanoborohydride (100 mg, 1.6 mmol) were stirred at ambient temperature in a 1% acetic acid/methanol solution (50 mL) for 18 h. The solvent was removed in vacuo. The residue was treated with 10% sodium carbonate solution and extracted with ethyl acetate. The ethyl acetate layer was separated and fumaric acid (0.14 g, 1.2 mmol) was added. After the solvent was removed in vacuo, the residue was triturated with hot methanol and allowed to cool overnight. The filtrate was collected, the solvent removed in vacuo. The residue was triturated with ethyl acetate overnight, collected by filtration, and dried to give [2-methoxy-3-(5-methyl-2-nitrophenoxy)benzyl]methylamine fumarate (195 mg, 38%) as a beige solid.

MS (APCI+) 303 [M+1]+.

$^1$H-NMR (300 MHz, d$_6$-DMSO): δ 7.98 (1H, d), 7.33 (1H, d), 7.20-7.10 (2H, m), 7.03 (1H, dd), 6.75 (1H, br s), 6.48 (2H, s), 3.90 (2H, s), 3.78 (3H, s), 2.42 (3H, s), 2.30 (3H, s).

EXAMPLE 44

4-Chloro-2-(3-dimethylaminomethyl-2-ethylphenoxy)benzonitrile fumarate a) (2-Ethyl-3-methoxybenzyl)dimethylamine (3-Methoxybenzyl)dimethylamine (2.03 mL, 2.00 g, 12.1 mmol) was dissolved in anhydrous THF (20 mL) under nitrogen and cooled to 0° C. with an ice-water bath. Butyllithium (2.5M in hexanes, 5.3 mL, 13.3 mmol) was added dropwise via syringe over 10 min (temperature kept below 5° C.). After stirring at 0° C. for 2 h, iodoethane (1.1 mL, 2.1 g, 13.8 mmol) was added dropwise via syringe over 25 min (temperature kept below 5° C.). The reaction mixture was allowed to reach ambient temperature. After 4 h, the reaction contents were transferred with diethyl ether and adsorbed onto silica gel (3.8 g) upon removal of the solvent in vacuo. Chromatography gave (2-ethyl-3-methoxybenzyl)dimethylamine (1.30 g, 56%) as a pale yellow solid.

MS (APCI+) 194 [M+1]+.

$^1$H-NMR (300 MHz, CDCl$_3$): δ 7.11 (1H, dd), 6.92 (1H, d), 6.78 (1H, d), 3.82 (3H, s), 3.39 (2H, s), 2.75 (2H, q), 2.24 (6H, s), 1.10 (3H, t).

b) 3-Dimethylaminomethyl-2-ethylphenol hydrobromide (2-Ethyl-3-methoxybenzyl)dimethylamine (1.30 g, 6.73 mmol) was suspended in 30% hydrogen bromide/acetic acid (10 mL) and heated to reflux with stirring for 21 h. The cooled reaction mixture was triturated and decanted with successive portions of diethyl ether (3×), then triturated with diethyl ether overnight. The solid was collected by filtration, washed with ether and dried to give 3-dimethylaminomethyl-2-ethylphenol hydrobromide (1.37 g, 78%) as a tan solid.

MS (APCI+) 180 [M+1]+.

$^1$H-NMR (300 MHz, d$_6$-DMSO): δ 9.56 (1H, s), 9.30 (1H, br s), 7.10 (1H, dd), 6.93 (1H, d), 6.89 (1H, d), 4.27 (2H, d), 2.77 (6H, d), 2.67 (2H, q), 1.04 (3H, t).

c) 4-Chloro-2-(3-dimethylaminomethyl-2-ethylphenoxy)benzonitrile fumarate

4-Chloro-2-fluorobenzonitrile (0.82 g, 5.27 mmol), 3-dimethylaminomethyl-2-ethylphenol hydrobromide (1.37 g, 5.27 mmol) and cesium carbonate (3.43 g, 10.5 mmol) were heated with stirring in dry DMF (8 mL) at 50° C. for 4 h. The reaction mixture was cooled, poured into 0.1N sodium hydroxide solution and extracted with diethyl ether. The ether layer was separated, washed with 1N sodium hydroxide solution (2×), water (3×), brine (1×), and dried over MgSO$_4$. After filtration, the solvent was removed in vacuo to give a yellow oil (1.86 g), which was purified by chromatography to yield 4-chloro-2-(3-dimethylaminomethyl-2-ethylphenoxy)benzonitrile (1.29 g, 78%) as a pale yellow oil. A small portion (98 mg) was converted into the fumarate salt (80 mg, 60%).

MS (APCI+) 315 [M+1]$^+$.

$^1$H-NMR (300 MHz, d$_6$-DMSO): δ 7.96 (1H, d), 7.35 (1H, dd), 7.32-7.23 (2H, m), 7.06 (1H, dd), 6.76 (1H, d), 6.62 (2H, s), 3.49 (2H, s), 2.64 (2H, q), 2.21 (6H, s), 1.08 (3H, t).

EXAMPLE 45

2-(3-Aminomethyl-2-ethyl-phenoxy)-4-chloro-benzonitrile hemifumarate a) 4-Chloro-2-(3-chloromethyl-2-ethyl-phenoxy)-benzonitrile 4-Chloro-2-(3-dimethylaminomethyl-2-ethylphenoxy) benzonitrile (1.18 g, 3.75 mmol) was dissolved in dry toluene (20 mL) and cooled to 0° C. with an ice-water bath. Ethyl chloroformate (1.08 mL, 1.22 g, 11.2 mmol) was added dropwise with stirring over 5 min (a white precipitate formed). The reaction mixture was allowed to reach ambient temperature, stirred for 19 h, poured into water, and extracted with diethyl ether. The ether layer was washed with water (2×), brine (1×), and dried over MgSO$_4$. After filtration, the solvent was removed in vacuo to give a pale yellow oil (0.89 g), which was purified by chromatography to give 4-chloro-2-(3-chloromethyl-2-ethyl-phenoxy)-benzonitrile (0.71 g, 62%) as a colourless oil which later solidified.

$^1$H-NMR (300 MHz, d$_6$-DMSO): δ 7.98 (1H, d), 7.43-7.30 (3H, m), 7.14 (1H, d), 6.83 (1H, d), 4.87 (2H, s), 2.68 (2H, q), 1.15 (3H, t).

b) 2-(3-Aminomethyl-2-ethyl-phenoxy)-4-chloro-benzonitrile hemifumarate

To a solution of 4-chloro-2-(3-chloromethyl-2-ethyl-phenoxy)-benzonitrile (0.16 g, 0.53 mmol) in methanol (10 mL) was added ammonia (7N in methanol, 15 mL, 105 mmol), and the reaction mixture stirred for 4 days at ambient temperature. The solvent was removed in vacuo. The residue was treated with 10% sodium carbonate solution and extracted with ethyl acetate. The ethyl acetate layer was separated and a solution of fumaric acid (60 mg, 0.52 mmol) in methanol (3 mL) was added. After the solvent was removed in vacuo, the residue was triturated with diethyl ether overnight, collected by filtration, and dried to give 2-(3-aminomethyl-2-ethyl-phenoxy)-4-chloro-benzonitrile hemifumarate (174 mg, 83%) as a white solid.

MS (APCI+) 287/289 [M+1]$^+$.

$^1$H-NMR (300 MHz, d$_6$-DMSO): δ 8.24 (2H, br s), 7.99 (1H, d), 7.47-7.33 (3H, m), 7.19 (1H, br d), 6.76 (1H, s), 6.63 (1H, s), 4.14 (2H, br s), 2.62 (2H, q), 1.08 (3H, t).

EXAMPLE 46

4-Chloro-2-(2-ethyl-3-methylaminomethyl-phenoxy)-benzonitrile fumarate

To a solution of 4-chloro-2-(3-chloromethyl-2-ethyl-phenoxy)-benzonitrile (0.39 g, 1.3 mmol) in ethanol (20 mL) was added methylamine (33% in ethanol, 5.0 mL, 40 mmol), and the reaction mixture stirred for 24 h at ambient temperature. The solvent was removed in vacuo. The residue was treated with 10% sodium carbonate solution and extracted with ethyl acetate. The ethyl acetate layer was separated and a solution of fumaric acid (148 mg, 1.3 mmol) in methanol (5 mL) was added. After the solvent was removed in vacuo, the residue was triturated with diethyl ether overnight, collected by filtration, and dried to give 4-chloro-2-(2-ethyl-3-methylaminomethyl-phenoxy)-benzonitrile fumarate (455 mg, 86%) as a white solid.

MS (APCI+) 301/303 [M+1]$^+$.

$^1$H-NMR (300 MHz, d$_6$-DMSO): δ 7.98 (1H, d), 7.43-7.30 (3H, m), 7.12 (1H, d), 6.76 (1H, d), 6.51 (2H, s), 3.97 (2H, s), 2.62 (2H, q), 2.50 (3H, s), 1.07 (3H, t).

EXAMPLE 47

4-Chloro-2-(3-dimethylaminomethyl-2-propylphenoxy)-benzonitrile fumarate a) (3-Methoxy-2-propylbenzyl)-dimethylamine (3-Methoxybenzyl)dimethylamine (2.03 mL, 2.00 g, 12.1 mmol) was dissolved in anhydrous THF (20 mL) under nitrogen and cooled to 0° C. with an ice-water bath. Butyllithium (2.5M in hexanes, 5.1 mL, 12.7 mmol) was added dropwise via syringe over 20 min (temperature kept below 5° C.). After stirring at 0° C. for 2 h, 1-iodopropane (1.25 mL, 2.18 g, 12.8 mmol) was added dropwise via syringe over 15 min (temperature kept below 5° C.). The reaction mixture was allowed to reach ambient temperature. After 23 h, water (~10 mL) was added, and the organic solvent was removed in vacuo. The residue was extracted with diethyl ether, washed with water (2×), brine (1×) and dried over MgSO$_4$. After filtration, the solvent was removed in vacuo to give a colourless oil (2.25 g), which was purified by chromatography to give (3-methoxy-2-propylbenzyl)-dimethylamine (1.52 g, 62%) as a colourless oil.

MS (APCI+) 208 [M+1]$^+$.

$^1$H-NMR (300 MHz, CDCl$_3$): δ 7.10 (1H, dd), 6.92 (1H, d), 6.77 (1H, d), 3.80 (3H, s), 3.38 (2H, s), 2.73-2.64 (2H, m), 2.23 (6H, s), 1.58-1.43 (2H, m), 0.97 (3H, t).

b) 3-Dimethylaminomethyl-2-propylphenol hydrobromide (3-Methoxy-2-propylbenzyl)-dimethylamine (1.51 g, 7.28 mmol) was suspended in 30% hydrogen bromide/acetic acid (10 mL) and heated to reflux with stirring for 20 h. The cooled reaction mixture was triturated and decanted with successive portions of diethyl ether (4×), then triturated with diethyl ether overnight. The solid was collected by filtration, washed with ether and dried to give 3-dimethylaminomethyl-2-propylphenol hydrobromide (1.58 g, 79%) as a tan solid.

MS (APCI+) 194 [M+1]$^+$.

$^1$H-NMR (300 MHz, CDCl$_3$): δ 9.54 (1H, s), 9.28 (1H, br s), 7.10 (1H, dd), 6.94 (1H, d), 6.89 (1H, d), 4.27 (2H, d), 2.77 (6H, d), 2.66-2.57 (2H, m), 1.51-1.35 (2H, m), 0.93 (3H, t).

c) 4-Chloro-2-(3-dimethylaminomethyl-2-propylphenoxy)-benzonitrile fumarate

4-Chloro-2-fluorobenzonitrile (0.90 g, 5.8 mmol), 3-dimethylaminomethyl-2-propylphenol hydrobromide (1.58 g, 5.8 mmol) and cesium carbonate (3.94 g, 12.1 mmol) were heated with stirring in dry DMF (6 mL) at 50° C. for 18 h. The reaction mixture was cooled, poured into 0.1N sodium hydroxide solution and extracted with diethyl ether. The ether layer was separated, washed with 1N sodium hydroxide solution (1×), water (2×), brine (1×), and dried over MgSO$_4$. After filtration, the solvent was removed in vacuo to give a yellow oil (1.77 g), which was purified by chromatography to yield 4-chloro-2-(3-dimethylaminomethyl-2-propylphenoxy)-benzonitrile (1.53 g, 81%) as a pale yellow oil. A small portion (100 mg) was converted into the fumarate salt (63 mg, 47%).

MS (APCI+) 329/331 [M+1]$^+$.

$^1$H-NMR (300 MHz, d$_6$-DMSO): δ 7.96 (1H, d), 7.35 (1H, br dd), 7.31-7.24 (2H, m), 7.07 (1H, dd), 6.74 (1H, br d), 6.62 (2H, s), 3.49 (2H, s), 2.62-2.53 (2H, m), 2.22 (6H, s), 1.56-1.41 (2H, m), 0.89 (3H, t).

EXAMPLE 48

2-(3-Aminomethyl-2-propyl-phenoxy)-4-chloro-benzonitrile hemifumarate a) 4-Chloro-2-(3-chloromethyl-2-propylphenoxy)-benzonitrile 4-Chloro-2-(3-dimethylaminomethyl-2-propylphenoxy)-benzonitrile (1.40 g, 4.26 mmol) was dissolved in dry toluene (20 mL) and cooled to 0° C. with an ice-water bath. Ethyl chloroformate (1.25 mL, 1.42 g, 13.1 mmol) was added dropwise with stirring over 5 min (a white precipitate formed). The reaction mixture was allowed to reach ambient temperature, stirred 18 h, poured into water, and extracted with diethyl ether. The ether layer was washed with water (2×), brine (1×), and dried over MgSO$_4$. After filtration, the solvent was removed in vacuo to give a pale yellow oil (1.05 g), which was purified by chromatography to give 4-chloro-2-(3-chloromethyl-2-propylphenoxy)-benzonitrile (0.83 g, 61%) as a white solid.

$^1$H-NMR (300 MHz, CDCl$_3$): δ 7.60 (1H, d), 7.34-7.22 (2H, m), 7.11 (1H, dd), 6.97 (1H, dd), 6.74 (1H, d), 4.66 (2H, s), 2.70-2.62 (2H, m), 1.69-1.55 (2H, m), 0.99 (3H, t).

b) 2-(3-Aminomethyl-2-propyl-phenoxy)-4-chloro-benzonitrile hemifumarate

4-Chloro-2-(3-chloromethyl-2-propylphenoxy)-benzonitrile (0.16 g, 0.50 mmol) in ammonia (7N in methanol, 25 mL, 175 mmol) was stirred for 65 h at ambient temperature. The solvent was removed in vacuo. The residue was treated with 10% sodium carbonate solution and extracted with ethyl acetate. The ethyl acetate layer was separated and a solution of fumaric acid (58 mg, 0.50 mmol) in methanol (3 mL) was added. After the solvent was removed in vacuo, the residue was triturated with diethyl ether overnight, collected by filtration, and dried to give 2-(3-aminomethyl-2-propyl-phenoxy)-4-chloro-benzonitrile hemifumarate (200 mg, 96%) as a white solid.

MS (APCI+) 301/303 [M+1]$^+$.

$^1$H-NMR (300 MHz, d$_6$-DMSO): δ 8.23 (2H, br s), 7.99 (1H, d), 7.47-7.34 (3H, m), 7.21 (1H, br d), 6.74 (1H, s), 6.63 (1H, s), 4.13 (2H, br s), 2.61-2.52 (2H, m), 1.55-1.40 (2H, m), 0.91 (3H, t).

EXAMPLE 49

4-Chloro-2-(3-methylaminomethyl-2-propyl-phenoxy)-benzonitrile fumarate

To a solution of 4-chloro-2-(3-chloromethyl-2-propylphenoxy)-benzonitrile (0.35 g, 1.1 mmol) in ethanol (20 mL) was added methylamine (33% in ethanol, 9.0 mL, 72 mmol), and the reaction mixture stirred 18 h at ambient temperature. The solvent was removed in vacuo. The residue was treated with 10% sodium carbonate solution and extracted with ethyl acetate. The ethyl acetate layer was separated and a solution of fumaric acid (127 mg, 1.1 mmol) in methanol (5 mL) was added. After the solvent was removed in vacuo, the residue was triturated with diethyl ether overnight, collected by filtration, and dried to give 4-chloro-2-(3-methylaminomethyl-2-propyl-phenoxy)-benzonitrile fumarate (354 mg, 75%) as a white solid.

MS (APCI+) 315/317 [M+1]$^+$.

$^1$H-NMR (300 MHz, d$_6$-DMSO): δ 7.97 (1H, d), 7.43-7.29 (3H, m), 7.11 (1H, d), 6.73 (1H, br s), 6.50 (2H, s), 3.91 (2H, s), 2.60-2.51 (2H, m), 2.46 (3H, s), 1.54-1.39 (2H, m), 0.89 (3H, t).

EXAMPLE 50

2-(2-Allyl-4-methylaminomethyl-phenoxy)-4-chlorobenzonitrile fumarate a) 3-Allyl-4-hydroxybenzaldehyde 4-Allyloxybenzaldehyde (1.16 g, 7.15 mmol) in dry DMF (3 mL) was stirred at 170° C. for 30 h. The reaction mixture was cooled, poured into water and extracted with ethyl acetate. The ethyl acetate layer was extracted with 1N sodium hydroxide solution (2×). The basic extracts were combined and acidified by addition of 3N hydrochloric acid, then extracted with ethyl acetate. The ethyl acetate layer was washed with water (2×), brine (1×), and dried over MgSO$_4$. After filtration, the solvent was removed in vacuo to yield 3-allyl-4-hydroxybenzaldehyde (0.34 g, 29%) as a yellow oil.

MS (APCI+) 163 [M+1]$^+$.

$^1$H-NMR (300 MHz, CDCl$_3$): δ 9.85 (1H, s), 7.75-7.67 (2H, m), 6.95 (1H, d), 6.10-5.95 (1H, m), 5.24-5.20 (1H, m), 5.19-5.14 (1H, m), 3.47 (2H, br d).

b) 2-(2-Allyl-4-formyl-phenoxy)-4-chlorobenzonitrile

4-Chloro-2-fluorobenzonitrile (0.34 g, 2.2 mmol), 3-allyl-4-hydroxybenzaldehyde (0.34 g, 2.1 mmol) and potassium fluoride (0.37 g, 6.3 mmol) were heated with stirring in dry DMF (4 mL) at 120° C. for 4 h. The reaction mixture was cooled, poured into 0.1N sodium hydroxide solution and extracted with ethyl acetate. The ethyl acetate layer was separated, washed with 0.1N sodium hydroxide solution (3×), water (2×), brine (1×), and dried over MgSO$_4$. After filtration, the solvent was removed in vacuo and the residue purified by chromatography to give 2-(2-allyl-4-formyl-phenoxy)-4-chlorobenzonitrile (0.09 g, 15%) as a colourless oil.

$^1$H-NMR (300 MHz, CDCl$_3$): δ 10.00 (1H, s), 7.89 (1H, br d), 7.80 (1H, dd), 7.67-7.56 (1H, m), 7.28 (1H, d), 7.05 (1H, d), 6.84 (1H, d), 6.04-5.88 (1H, m), 5.18-5.06 (2H, m), 3.49 (2H, d).

c) 2-(2-Allyl-4-methylaminomethyl-phenoxy)-4-chlorobenzonitrile fumarate 2-(2-Allyl-4-formyl-phenoxy)-4-chlorobenzonitrile (0.09 g, 0.30 mmol), methylamine (33% in ethanol, 0.3 mL, 2.4 mmol) and sodium cyanoborohydride (40 mg, 0.64 mmol) were stirred at ambient temperature in a solution of glacial acetic acid (0.5 mL) in methanol (25 mL) for 20 h. The solvent was removed in vacuo. The residue was treated with 10% sodium carbonate solution and extracted with ethyl acetate. The ethyl acetate layer was separated and fumaric acid (36 mg, 0.30 mmol) was added. After the solvent was removed in vacuo, the residue was triturated with ethyl acetate overnight, collected by filtration, and dried to give 2-(2-allyl-4-methylaminomethyl-phenoxy)-4-chlorobenzonitrile fumarate (104 mg, 80%) as a white solid.

MS (APCI+) 313/315 [M+1]+.

$^1$H-NMR (300 MHz, $d_6$-DMSO): δ 7.97 (1H, d), 7.52 (1H, s), 7.46 (1H, s), 7.38 (1H, d), 7.23 (1H, d), 6.79 (1H, d), 6.65 (2H, s), 5.97-5.85 (1H, m), 5.08-5.02 (2H, m), 4.16 (2H, s), 3.36 (2H, d), 2.60 (3H, s).

EXAMPLE 51

4-Chloro-2-(3-dimethylaminomethyl-4-fluorophenoxy)benzonitrile a) (2-Fluoro-5-methoxybenzyl)dimethylamine 2-Fluoro-5-methoxybenzaldehyde (2.62 g, 17.0 mmol), dimethylamine (2M in methanol, 17 mL, 34 mmol) and sodium cyanoborohydride (1.17 g, 18.7 mmol) were stirred at ambient temperature in a solution of glacial acetic acid (2 mL) in methanol (100 mL) for 66 h. The solvent was removed in vacuo. The residue was treated with 10% sodium carbonate solution and extracted with ethyl acetate. The ethyl acetate layer was washed with water (2×), brine (1×), and dried over MgSO$_4$. After filtration, the solvent was removed in vacuo to give (2-fluoro-5-methoxybenzyl)dimethylamine (3.02 g, 97%) as a yellow oil.

MS (APCI+) 184 [M+1]+.

$^1$H-NMR (300 MHz, CDCl$_3$): δ 6.98-6.86 (2H, m), 6.78-6.71 (1H, m), 3.78 (3H, s), 3.46 (2H, s), 2.27 (6H, s).

b) 3-Dimethylaminomethyl-4-fluorophenol hydrobromide (2-Fluoro-5-methoxybenzyl)-dimethylamine (1.51 g, 8.24 mmol) was heated to reflux in 30% hydrogen bromide/acetic acid (10 mL) for 17 h. The cooled reaction mixture was triturated and decanted with successive portions of diethyl ether (4×), then triturated with diethyl ether overnight. The solid was collected by filtration, washed with ether and dried to give 3-dimethylaminomethyl-4-fluorophenol hydrobromide (1.43 g, 69%) as a tan solid.

MS (APCI+) 170 [M+1]+.

$^1$H-NMR (300 MHz, $d_6$-DMSO): δ 9.68 (1H, s), 7.18-7.10 (1H, m), 6.98-6.93 (1H, m), 6.92-6.85 (1H, m), 4.26 (2H, s), 2.76 (6H, s).

c) 4-Chloro-2-(3-dimethylaminomethyl-4-fluorophenoxy)benzonitrile

4-Chloro-2-fluorobenzonitrile (0.48 g, 3.1 mmol), 3-dimethylaminomethyl-4-fluorophenol hydrobromide (0.74 g, 3.0 mmol) and cesium carbonate (2.02 g, 6.2 mmol) were heated with stirring in dry DMF (5 mL) at 50° C. for 18 h. The reaction mixture was cooled, poured into 0.1N sodium hydroxide solution and extracted with diethyl ether. The ether layer was separated, washed with 1N sodium hydroxide solution (2×), water (2×), brine (1×), and dried over MgSO$_4$. After filtration, the solvent was removed in vacuo to give a yellow oil (0.93 g), which was purified by chromatography to yield 4-chloro-2-(3-dimethylaminomethyl-4-fluorophenoxy)benzonitrile (0.68 g, 76%) as a pale yellow oil.

MS (APCI+) 305/307 [M+1]+.

$^1$H-NMR (300 MHz, CDCl$_3$): δ 7.57 (1H, d), 7.21-7.07 (3H, m), 7.02-6.95 (1H, m), 6.75 (1H, br s), 3.50 (2H, s), 2.28 (6H, s).

EXAMPLE 52

4-Chloro-2-(4-fluoro-3-methylaminomethyl-phenoxy)-benzonitrile fumarate a) 4-Chloro-2-(3-chloromethyl-4-fluorophenoxy)-benzonitrile 4-Chloro-2-(3-dimethylaminomethyl-4-fluorophenoxy)benzonitrile (0.56 g, 1.8 mmol) was dissolved in dry toluene (12 mL) and cooled to 0° C. with an ice-water bath. Ethyl chloroformate (0.55 mL, 0.62 g, 5.8 mmol) was added dropwise with stirring over 5 min. The reaction mixture was allowed to reach ambient temperature, stirred 20 h, poured into water, and extracted with diethyl ether. The ether layer was washed with water (2×), brine (1×), and dried over MgSO$_4$. After filtration, the solvent was removed in vacuo to give a pale yellow oil (0.39 g), which was purified by chromatography to give 4-chloro-2-(3-chloromethyl-4-fluorophenoxy)-benzonitrile (0.14 g, 26%) as a white solid.

$^1$H-NMR (300 MHz, CDCl$_3$): δ 7.60 (1H, d), 7.24-7.12 (3H, m), 7.09-7.02 (1H, m), 6.80 (1H, d), 4.63 (2H, s).

b) 4-Chloro-2-(4-fluoro-3-methylaminomethyl-phenoxy)-benzonitrile fumarate

To a solution of 4-chloro-2-(3-chloromethyl-4-fluorophenoxy)-benzonitrile (0.14 g, 0.47 mmol) in ethanol (15 mL) was added methylamine (33% in ethanol, 4.0 mL, 32 mmol), and the reaction mixture stirred for 10 days at ambient temperature. The solvent was removed in vacuo. The residue was treated with 10% sodium carbonate solution and extracted with ethyl acetate. The ethyl acetate layer was separated and a solution of fumaric acid (50 mg, 0.43 mmol) in methanol (3 mL) was added. After the solvent was removed in vacuo, the residue was triturated with diethyl ether overnight, collected by filtration, and dried to give 4-chloro-2-(4-fluoro-3-methylaminomethyl-phenoxy)-benzonitrile fumarate (183 mg, 95%) as a white solid.

MS (APCI+) 291/293 [M+1]+.

$^1$H-NMR (300 MHz, $d_6$-DMSO): δ 7.95 (1H, d), 7.38 (1H, dd), 7.33-7.27 (2H, m), 7.23-7.15 (1H, m), 6.93 (1H, m), 6.45 (1H, s), 3.74 (2H, s), 2.29 (3H, s).

EXAMPLE 53

2-(2-Methoxy-3-methylaminomethyl-phenoxy)-4-trifluoromethyl-benzonitrile fumarate a) 2-(3-Formyl-2-methoxy-phenoxy)-4-trifluoromethyl-benzonitrile 2-Fluoro-4-trifluoromethyl-benzonitrile (0.56 mL, 0.76 g, 4 mmol), 3-hydroxy-2-methoxybenzaldehyde (0.61 g, 4 mmol) and cesium carbonate (1.3 g, 4 mmol) were heated with stirring in dry DMF (4 mL) at 50° C. for 18 h. The reaction mixture was cooled, poured into water and extracted with ethyl acetate. The ethyl acetate layer was separated, washed with water (2×), 10% sodium carbonate solution (2×), water (1×), brine (1×), and dried over MgSO$_4$. After filtration, the solvent was removed in vacuo to yield 2-(3-formyl-2-methoxy-phenoxy)-4-trifluoromethyl-benzonitrile (1.17 g, 91%) as a brown solid.

$^1$H-NMR (300 MHz, d$_6$-DMSO): δ 10.30 (1H, s), 8.21 (1H, d), 7.63 (3H, m), 7.39 (1H, m), 7.18 (1H, s), 3.93 (3H, s).

b) 2-(2-Methoxy-3-methylaminomethyl-phenoxy)-4-trifluoromethyl-benzonitrile fumarate 2-(3-Formyl-2-methoxy-phenoxy)-4-trifluoromethyl-benzonitrile (0.46 g, 1.43 mmol), methylamine (2M in methanol, 22.2 mL, 4.4 mmol) and sodium cyanoborohydride (0.13 g, 2.1 mmol) were stirred at ambient temperature in a 1% acetic acid/methanol solution (70 mL) for 20 h. The solvent was removed in vacuo. The residue was treated with 10% sodium carbonate solution and extracted with ethyl acetate. Fumaric acid (0.15 g, 1.3 mmol) was added to the separated ethyl acetate layer and the solvent removed in vacuo. The residue was triturated with diethyl ether overnight, filtered and dried to give 2-(2-methoxy-3-methylaminomethyl-phenoxy)-4-trifluoromethyl-benzonitrile fumarate (179 mg, 28%) as a white solid.

MS (APCI+) 337 [M+1]$^+$.

$^1$H-NMR (300 MHz, d$_6$-DMSO): δ 8.22 (1H, d), 7.67 (1H, d), 7.43 (1H, d), 7.28 (2H, m), 6.97 (1H, s), 6.51 (2H, s), 3.93 (2H, s), 3.79 (3H, s), 2.42 (3H, s).

EXAMPLE 54

2-(4-methylaminomethyl-3-phenyl-phenoxy)-4-trifluoromethyl-benzonitrile fumarate a) 2-(3-Bromo-4-formyl-phenoxy)-4-trifluoromethyl-benzonitrile 2-Fluoro-4-trifluoromethyl-benzonitrile (3.1 g, 20 mmol), 2-bromo-4-hydroxybenzaldehyde (4 g, 20 mmol) and potassium fluoride (3.47 g, 60 mmol) were heated with stirring in dry DMF (20 mL) at 120° C. for 4 h, 80° C. for 16 h, 120° C. for 4 h, 130° C. for 1 h, and then at 140° C. for 16 h. The reaction mixture was cooled, poured onto 1N sodium hydroxide, extracted with ethyl acetate, and then dried over MgSO$_4$. After filtration, the solvent was removed in vacuo to yield 2-(3-bromo-4-formyl-phenoxy)-4-trifluoromethyl-benzonitrile (6.38 g, 96%) as a brown oil.

b) 2-(4-Formyl-3-phenyl-phenoxy)-4-trifluoromethyl-benzonitrile

Under nitrogen, 2-(3-bromo-4-formyl-phenoxy)-4-trifluoromethyl-benzonitrile (0.87 g, 2.6 mmol), phenylboronic acid (336 mg, 2.7 mmol), 1,1'-bis(diphenyl)phosphino-ferrocene palladium (9 mg, 0.13 mmol) and sodium carbonate (331 mg, 3.1 mmol) in dimethoxyethane:water:ethanol solution (7:3:2, 10 mL) was stirred at 60° C. for 6 h and then at 40° C. for 16 h. The mixture was then poured over water, extracted into ethyl acetate, and dried over MgSO$_4$. The crude material was chromatographed on an ISCO Combi-Flash Chromatography System to yield 2-(4-formyl-2-methoxy-phenoxy)-4-trifluoromethyl-benzonitrile as a clear oil (117 mg, 14%).

c) 2-(4-methylaminomethyl-3-phenyl-phenoxy)-4-trifluoromethyl-benzonitrile fumarate 2-(4-Formyl-3-phenyl-phenoxy)-4-trifluoromethyl-benzonitrile (0.117 g, 0.35 mmol), methylamine (2M in methanol, 0.233 mL, 1.05 mmol) and sodium cyanoborohydride (0.025 g, 0.39 mmol) were stirred at ambient temperature in a 1% acetic acid/methanol solution for 20 h. The solvent was removed in vacuo. The residue was treated with 10% sodium carbonate solution and extracted with ethyl acetate. Fumaric acid (0.032 g, 0.28 mmol) was added to the separated ethyl acetate layer and the solvent removed in vacuo. The residue was triturated with ethyl acetate overnight, filtered and dried to give 2-(4-methylaminomethyl-3-phenyl-phenoxy)-4-trifluoromethyl-benzonitrile fumarate (75 mg, 61%) as a white solid.

MS (APCI+) 350 [M+1]$^+$.

$^1$H-NMR (300 MHz, d$_6$-DMSO): δ 7.67 (1H, d), 7.59 (2H, m), 7.51 (2H, m), 7.33 (3H, m) 7.09 (1H, dd), 6.68 (2H, s), 6.62 (1H, d), 4.26 (2H, s), 2.77 (3H, s).

EXAMPLE 55

4-Chloro-2-(3-dimethylaminomethyl-2-methysulfanyl-phenoxy)-benzonitrile fumarate a) (2-Methylsulfanyl-3-methoxybenzyl)-dimethylamine Under a nitrogen atmosphere, 3-methoxy-N,N-dimethylbenzylamine (2.00 g, 12.1 mmol) was dissolved in anhydrous THF (20 mL) and cooled to 0° C. in an ice bath. 2.5M n-butyl lithium in hexanes (5.3 mL, 13.3 mmol) was added slowly, maintaining the temperature to below 5° C. The reaction was stirred at 0° C. for 2 h, then dimethyldisulfide (1.59 g, 13 mmol) was slowly added over 90 min, maintaining the temperature to below 5° C. The reaction mixture was stirred for 17 h, during which time the temperature was allowed to reach room temperature. Water (20 mL) and diethyl ether (30 mL) were added and the organic layer was separated and dried with MgSO$_4$. After filtration, the crude solution was dissolved in ethyl acetate and absorbed in vacuo onto silica gel (1.5 g). This material was chromatographed on an ISCO CombiFlash Chromatography System to yield (2-methylsulfanyl-3-methoxybenzyl)-dimethylamine as a yellow oil (1.47 g, 57%).

MS (APCI+) 212 [M+1]$^+$.

$^1$H-NMR (300 MHz, CDCl$_3$): δ 7.25 (1H, dd), 7.05 (1H, d), 6.80 (1H, d), 3.91 (3H, s), 3.70 (2H, s), 2.32 (3H, s), 2.26 (6H, s).

b) 3-Dimethylaminomethyl-2-methylsulfanyl-phenol hydrobromide

30% Hydrogen bromide in acetic acid (7 mL, 34 mmol) was added to (2-methylsulfanyl-3-methoxybenzyl)-dimethylamine (1.44 g, 6.8 mmol) and heated with stirring at 100° C. After 17 h, the reaction was complete by LC/MS analysis and was then allowed to cool to room temperature. Diethyl ether (100 mL) was added with stirring. After 20 min, the orange diethyl ether solution was decanted off. This was repeated until a tan solid precipitated. 3-Dimethylaminomethyl-2-methylsulfanyl-phenol hydrobromide (1.74 g, 90%) was filtered off as a brown solid.

MS (APCI+) 198 [M+1]$^+$.

$^1$H-NMR (300 MHz, CDCl$_3$): δ 10.18 (1H, s), 9.16 (1H, s), 7.28 (1H, t), 7.03 (2H, m), 4.48 (2H, d), 2.77 (6H, d), 2.30 (3H, s).

c) 4-Chloro-2-(3-dimethylaminomethyl-2-methysulfanyl-phenoxy)-benzonitrile fumarate 4-Chloro-2-fluorobenzonitrile (0.974 g, 6.26 mmol), 3-dimethylaminomethyl-2-methylsulfanyl-phenol hydrobromide (1.74 g, 6.26 mmol) and cesium carbonate (4.08 g, 12.5 mmol) were heated with stirring in dry DMF (4 mL) at 50° C. for 17 h. The reaction was complete by LC/MS analysis. The reaction mixture was cooled, poured into water and extracted with ethyl acetate. The ethyl acetate layer was separated, washed with water (1×), 10% sodium carbonate solution (2×), water (2×), brine (1×), and dried over $MgSO_4$. After filtration, the solvent was removed in vacuo to yield 4-chloro-2-(3-dimethylaminomethyl-2-methylsulfanyl-phenoxy)-benzonitrile (1.2 g, 58%) as a yellow oil. Fumaric acid (92 mg, 0.3 mmol) in methanol (5 mL) was added to 4-chloro-2-(3-dimethylaminomethyl-2-ethylsulfanyl-phenoxy)-benzonitrile (91 mg, 0.26 mmol). The solvent was removed in vacuo and diethyl ether (20 mL) was added with stirring. After 17 h, 4-chloro-2-(3-dimethylaminomethyl-2-methysulfanyl-phenoxy)-benzonitrile fumarate (63.2 mg, 47%) was filtered off as a white solid.

MS (APCI+) 334 $[M+1]^+$.

$^1$H-NMR (300 MHz, $d_6$-DMSO): δ 7.95 (1H, d), 7.43 (2H, m), 7.36 (1H, dd), 7.23 (1H, dd), 6.67 (1H, d), 6.61 (2H, s), 3.71 (2H, s), 2.32 (3H, s), 2.23 (6H, s).

EXAMPLE 56

4-Chloro-2-(3-aminomethyl-2-methysulfanyl-phenoxy)-benzonitrile fumarate a) 4-Chloro-2-(3-chloromethyl-2-methysulfanyl-phenoxy)-benzonitrile Under a nitrogen atmosphere, 4-chloro-2-(3-dimethylaminomethyl-2-methysulfanyl-phenoxy)-benzonitrile (1.02 g, 3.06 mmol) was dissolved in anhydrous toluene (10 mL). The solution was cooled to 0° C. and ethyl chloroformate (900 µL, 9.2 mmol) was slowly added. The reaction mixture was stirred for 17 h, allowing it to reach room temperature. Water (5 mL) and diethyl ether (5 mL) were added and the organic layer was separated and dried with $MgSO_4$. After filtration, the solution was absorbed onto silica gel (1.5 g) and the solvent was removed in vacuo. This material was chromatographed on an ISCO CombiFlash Chromatography System to yield 4-chloro-2-(3-chloromethyl-2-methysulfanyl-phenoxy)-benzonitrile as a clear oil (800 mg, 81%).

$^1$H-NMR (300 MHz, $CDCl_3$): δ 7.59 (1H, s), 7.45 (2H, m), 7.13 (2H, m), 6.59 (1H, d), 4.93 (2H, s), 2.48 (3H, s).

b) 4-Chloro-2-(3-aminomethyl-2-methysulfanyl-phenoxy)-benzonitrile fumarate

7N Ammonia in methanol (30 mL, 210 mmol) was added to 4-chloro-2-(3-chloromethyl-2-methylsulfanyl-phenoxy)-benzonitrile (240 mg, 0.8 mmol). After stirring for 17 h, TLC still showed some 4-chloro-2-(3-chloromethyl-2-methysulfanyl-phenoxy)-benzonitrile. The reaction mixture was concentrated to about 10 mL by evaporation in vacuo, concentrated ammonia (7 mL) was added and the mixture was heated with stirring at 60° C. for 17 h. Sodium carbonate solution (4 mL) and ethyl acetate (6 mL) were added and the organic layer was separated and dried with $MgSO_4$. To this, was added fumaric acid (84 mg, 0.64 mmol) in methanol (3 mL). Immediately, the solvent was removed in vacuo and diethyl ether (40 mL) was added to the residue. After stirring for 17 h, 4-chloro-2-(3-aminomethyl-2-methysulfanyl-phenoxy)-benzonitrile fumarate (134.7 mg, 53%) was filtered off as a white solid.

MS (APCI+) 305 $[M+1]^+$.

$^1$H-NMR (300 MHz, $d_6$-DMSO): δ 7.95 (1H, d), 7.53 (2H, d), 7.34 (1H, dd), 7.25 (2H, t), 6.68 (1H, d), 6.43 (2H, s), 4.15 (2H, s), 2.5 (6H, m), 2.35 (3H, s).

EXAMPLE 57

4-Chloro-2-(2-methylsulfanyl-3-methylaminomethyl-phenoxy)-benzonitrile fumarate

33% Methylamine in ethanol (6 mL, 48 mmol) was added to 4-chloro-2-(3-chloromethyl-2-methylsulfanyl-phenoxy)-benzonitrile (256 mg, 0.8 mmol). After stirring the solution for 17 h, the solvent was removed in vacuo. Sodium carbonate solution (4 mL) and ethyl acetate (6 mL) were added and the organic layer was separated and dried with $MgSO_4$. To this, was added fumaric acid (74 mg, 0.64 mmol) in methanol (3 mL). Immediately, the solvent was removed in vacuo and diethyl ether (40 mL) was added to the crude material. After stirring for 17 h, 4-chloro-2-(2-methylsulfanyl-3-methylaminomethyl-phenoxy)-benzonitrile fumarate (253 mg, 0.581 mmol, 73%) was filtered off as a white solid.

$^1$H-NMR (300 MHz, d-DMSO): δ 7.96 (1H, d), 7.51 (2H, d), 7.26 (2H, m), 6.99 (1H, s), 6.52 (2H, s), 4.12 (2H, s), 2.45 (3H, s), 2.34 (3H, s).

EXAMPLE 58

4-Chloro-2-(3-dimethylaminomethyl-2-ethylsulfanyl-phenoxy)-benzonitrile fumarate a) 3-Dimethylaminomethyl-2-ethylsulfanyl-phenol hydrobromide 30% Hydrogen bromide in acetic acid (3.6 mL, 18.05 mmol) was added to (2-ethylsulfanyl-3-methoxybenzyl)-dimethylamine (800 mg, 3.55 mmol) and the reaction mixture was heated with stirring at 100° C. After 17 h, the reaction was complete by LC/MS analysis and was then allowed to cool to room temperature. Diethyl ether (100 mL) was added with stirring and after 20 min the orange diethyl ether solution was decanted off. This procedure was repeated until a tan solid precipitated. 3-Dimethylaminomethyl-2-ethylsulfanyl-phenol hydrobromide (770 mg, 100%) was filtered off as a tan solid.

$^1$H-NMR (300 MHz, $CDCl_3$): δ 10.16 (1H,s), 7.30 (1H, t) 7.03 (2H, m), 4.48 (2H, d), 2.80 (2H m), 2.76 (6H, d) 1.05 (3H, t).

b) 4-Chloro-2-(3-dimethylaminomethyl-2-ethylsulfanyl-phenoxy)-benzonitrile fumarate 4-Chloro-2-fluorobenzonitrile (0.567 g, 3.6 mmol), 3-dimethylaminomethyl-2-ethylsulfanyl-phenol hydrobromide (0.77 g, 2.6 mmol) and cesium carbonate (1.19 g, 3.6 mmol) were heated with stirring in dry DMF (4 mL) at 50° C. for 17 h. More cesium carbonate (1.19 g, 3.6 mmol) was added. After 1 h, the reaction was complete by LC/MS analysis. The reaction mixture was cooled, poured into water and extracted with ethyl acetate. The ethyl acetate layer was separated, washed with water (1×), 10% sodium carbonate solution (2×), water (2×), brine (1×), and dried over $MgSO_4$. After filtration, the solvent was removed in vacuo to yield 4-chloro-2-(3-dimethylaminomethyl-2-ethylsulfanyl-phenoxy)-benzonitrile (662 mg, 52%) as a clear oil. Fumaric acid (30 mg, 0.26 mmol) in methanol (5 mL) was added to 4-chloro-2-(3-dimethylaminomethyl-2-ethylsulfanyl-phenoxy)-benzonitrile (91 mg, 0.26 mmol). The solvent was removed in vacuo and diethyl ether (20 mL) was added with stirring. After 17 h, 4-chloro-2-(3-dimethylaminomethyl-2-ethylsulfanyl-phenoxy)-benzonitrile fumarate (41.4 mg, 34%) was filtered off as a white solid.

MS (APCI+) 348 [M+1]$^+$.

$^1$H-NMR (300 MHz, d$_6$-DMSO): δ 7.94 (1H, d), 7.50 (2H, m), 7.23 (2H, dd), 6.61 (1H, s), 6.61 (2H, s), 3.71 (2H, s), 2.79 (3H, q), 2.22 (6H, s), 1.07 (3H, t).

EXAMPLE 59

4-Chloro-2-(3-aminomethyl-2-ethylsulfanyl-phenoxy)-benzonitrile fumarate a) 4-Chloro-2-(3-chloromethyl-2-ethylsulfanyl-phenoxy)-benzonitrile Under a nitrogen atmosphere, 4-chloro-2-(3-dimethylaminomethyl-2-ethylsulfanyl-phenoxy)-benzonitrile (570 mg, 1.64 mmol) was dissolved in anhydrous toluene (10 mL). The solution was cooled to 0° C. and ethyl chloroformate (480 µL, 5 mmol) was slowly added. The reaction mixture was stirred for 17 h, allowing it to reach room temperature. Water (5 mL) and diethyl ether (5 mL) were added and the organic layer was separated and dried with MgSO$_4$. After filtration, the solvent was removed in vacuo to yield crude material (340 mg) that was then dissolved in ethyl acetate and absorbed in vacuo onto silica gel (1.5 g). This material was chromatographed on an ISCO Combi-Flash Chromatography System to yield 4-chloro-2-(3-chloromethyl-2-ethylsulfanyl-phenoxy)-benzonitrile as a clear oil (240 mg, 43%).

$^1$H-NMR (300 MHz, CDCl$_3$): δ 7.58 (1H, d), 7.45 (2H, m), 7.11 (2H, m), 6.57 (1H, d), 4.94 (2H, s) 2.96 (2H, q), 1.22 (3H, t).

b) 4-Chloro-2-(3-aminomethyl-2-ethylsulfanyl-phenoxy)-benzonitrile fumarate

7N Ammonia in methanol (12 mL, 84 mmol) was added to 4-chloro-2-(3-chloromethyl-2-ethylsulfanyl-phenoxy)-benzonitrile (80 mg, 0.24 mmol). After stirring for 17 h, the solvent was removed in vacuo. Sodium carbonate solution (4 mL) and ethyl acetate (6 mL) were added and the organic layer was separated and dried with MgSO$_4$. To this, was added fumaric acid (22 mg, 0.19 mmol) in methanol (3 mL). Immediately, the solvent was removed in vacuo and diethyl ether (40 mL) was added to the crude material. After stirring for 17 h, 4-chloro-2-(3-aminomethyl-2-ethylsulfanyl-phenoxy)-benzonitrile fumarate (54.6 mg, 0.126 mmol, 53%) was filtered off as a white solid.

MS (APCI+) 320 [M+1]$^+$.

$^1$H-NMR (300 MHz, d$_6$-DMSO): δ 7.94 (1H, d), 7.49 (2H, m), 7.32 (1H, m), 7.21 (1H, dd), 6.60 (1H, m), 6.37 (1H, s), 4.01 (2H, s), 2.78 (2H, m), 1.06 (3H, t).

EXAMPLE 60

4-Chloro-2-(2-ethysulfanyl-3-methylaminomethyl-phenoxy)-benzonitrile fumarate

2M Methylamine in methanol (14 mL, 28 mmol) was added to 4-chloro-2-(3-chloromethyl-2-ethylsulfanyl-phenoxy)-benzonitrile (160 mg, 0.47 mmol). After stirring the solution for 17 h, the solvent was removed in vacuo. Sodium carbonate solution (4 mL) and ethyl acetate (6 mL) were added and the organic layer was separated and dried with MgSO$_4$. To this, was added fumaric acid (44 mg, 37.6 mmol) in methanol (3 mL). The solvent was immediately removed in vacuo and diethyl ether (40 mL) was added to the crude material. After stirring 17 h, 4-chloro-2-(2-ethylsulfanyl-3-methylaminomethyl-phenoxy)-benzonitrile fumarate (66.3 mg, 0.148 mmol, 31%) was filtered off as a white solid.

MS (APCI+) 334 [M+1]$^+$.

$^1$H-NMR (300 MHz, d$_6$-DMSO): δ 8.52 (1H, d), 7.95 (1H, d), 7.88 (1H, s), 7.5 (1H, m), 7.32 (1H, dd), 6.61 (1H d), 6.45 (2H, s), 3.99 (3H, s), 2.78 (2H, m), 2.36 (3H, s), 1.08 (3H, m).

Screens

The pharmacological activity of compounds according to the invention was tested in the following screens.

Screen 1

The activity of compounds of formula (I), or a pharmaceutically acceptable salt, may be screened for nitric oxide synthase inhibiting activity by a procedure based on that of Förstermann et al., Eur. J. Pharm., 1992, 225, 161-165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17-20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 µl of substrate cocktail (50 mM Tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 mCi L-[$^3$H] arginine) is added to wells of a 96 well filter plate (0.45 µM pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled L-Citrulline is separated from labelled L-arginine using Dowex AG-SOW. 150 µl of a 25% aqueous slurry of Dowex 50 W (Na$^+$ form) is added to the assay after which the whole is filtered into 96 well plates. 75 µl of filtrate is sampled and added to wells of 96 well plates containing solid scintillant. After allowing the samples to dry the L-Citrulline is quantified by scintillation counting.

In a typical experiment basal activity is 300 dpm per 75 µl sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 µM, is tested as a standard to verify the procedure. Compounds are tested at a range of concentrations and from the inhibitions obtained $IC_{50}$ values are calculated. Compounds that inhibit the enzyme by at least 25% at 100 µM are classed as being active and are subjected to at least one retest.

Screen 2

Recombinant human NO synthases (iNOS, eNOS & nNOS) were expressed in E. coli and lysates were prepared in Hepes buffer (pH 7.4) containing co-factors (FAD, FMN, $H_4B$), protease inhibitors, lysozyme and the detergent, CHAPS. These preparations were used, at suitable dilution, to assess inhibition of the various isoforms. Inhibition of NOS was determined by measuring the formation of L-[$^3$H] citrulline from L-[$^3$H]arginine using an adaptation of the method of Förstermann et al. Enzyme assays were performed in the presence of 3 µM [$^3$H]arginine, 1 mM NADPH and other co-factors required to support NOS activity (FAD, FMN, $H_4B$, calmodulin, $Ca^{2+}$). Since various NOS inhibitors have been reported to exhibit slow binding kinetics, or to inactivate the enzyme in a time dependent manner, enzyme and inhibitor were pre-incubated for 60 min in the presence of NADPH before addition of arginine to initiate the reaction. Incubations continued for a further 60 min before the assays were quenched and [$^3$H]citrulline separated from unreacted substrate by chromatography on Dowex-50 W resin in a 96-well format.

In the above screen, the compounds of Examples 1 to 60 were tested and gave $IC_{50}$ values of less than 10 µM against the iNOS and nNOS enzymes, and showed good selectivity with respect to the inhibition of eNOS, indicating that they are expected to show useful therapeutic activity. Specimen results are shown in the following Table:

| Compound | $IC_{50}$ (µM) | | |
| --- | --- | --- | --- |
| | nNOS | eNOS | iNOS |
| Example 10 | 0.0048 | 0.34 | 0.0029 |
| Example 24 | 0.039 | 5.4 | 0.16 |
| Example 25 | 0.20 | 44 | 0.09 |

Screen 3

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10% (v/v) foetal bovine serum, and 2 mM L-glutamine, at 37° C. in 5% $CO_2$.

Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% $CO_2$ in RPMI 1640 containing 100 µM L-arginine and 100 µM verapamil-HCl in the presence and absence of test compounds.

Nitrite accumulation was determined by mixing an equal volume of culture media with Griess reagent (10 mg/ml sulphanilamide, 1 mg N-(1-naphthyl)ethylenediamine in 1 ml 2.5% (v/v) phosphoric acid). Inhibition in the presence of compounds was calculated relative to the nitrite levels produced by untreated cells. $IC_{50}$ values were estimated from a semi-log plot of % inhibition versus concentration of compound.

We claim:

1. A compound of formula (I)

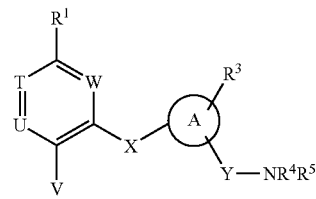

(I)

wherein:
A represents a phenyl ring or A represents a C8 to 10 aromatic or partially aromatic bicyclic ring system;
$R^1$ represents C1 to 6 alkyl, C1 to 6 alkoxy, halogen, hydroxy, cyano, trifluoromethyl or $NR^6R^7$;
$R^3$ represents hydrogen, C1 to 6 alkyl, C2 to 6 alkenyl, C3 to 6 cycloalkyl, C1 to 6 alkylthio, C1 to 6 alkoxy, halogen, hydroxy, cyano, trifluoromethyl or $NR^8R^9$, said alkoxy group being optionally further substituted by hydroxy or by one or more fluorine atoms;
or $R^3$ represents phenyl or a five- or six-membered aromatic heterocyclic ring containing 1 to 3 heteroatoms independently selected from O, S and N, said phenyl or aromatic heterocyclic ring being optionally substituted by one or more substituents selected independently from halogen, C1 to 4 alkyl, C1 to 4 alkoxy, hydroxy, cyano or $NR^8R^9$, said alkyl or alkoxy group being optionally further substituted by one or more fluorine atoms;
$R^4$ and $R^5$ independently represent hydrogen or C1 to 6 alkyl, said alkyl group being optionally substituted by OH, C1 to 6 alkoxy, $NR^{10}R^{11}$ or phenyl, said phenyl group being optionally further substituted by C1 to 6 alkyl, C1 to 6 alkoxy, halogen, hydroxy, cyano or $NR^{12}R^{13}$;
$R^6$, $R^7$, $R^8$, $R^9$, $R^{10}$, $R^{11}$, $R^{12}$ and $R^{13}$ independently represent hydrogen or C1 to 6 alkyl, said alkyl group being optionally substituted by OH or C1 to 6 alkoxy;
or the groups $NR^4R^5$, $NR^6R^7$ and $NR^8R^9$ independently represent a 4- to 7-membered saturated azacyclic ring optionally incorporating one further heteroatom selected from O or N, said ring being optionally substituted by OH, C1 to 3 hydroxyalkyl or C1 to 3 alkoxy;
V represents cyano or nitro;
X represents O or $S(O)_n$;
n represents an integer 0, 1 or 2;
Y represents C1 to 6 alkyl;
any one of T, U and W represents N and the other two independently represent $CR^2$ and each $R^2$ group independently represents hydrogen, C1 to 3 alkyl, C1 to 3 alkoxy or halogen;
or a pharmaceutically acceptable salt thereof.

2. A compound of formula (I), according to claim 1, wherein A represents phenyl.

3. A compound of formula (I), according to claim 1, wherein Y represents $CH_2$.

4. A compound of formula (I), according to claim 1, wherein $R^4$ and $R^5$ independently represent hydrogen or methyl.

5. A compound of formula (I), according to claim 1, which is:
- 2-(2-methoxy-3-methylaminomethyl-phenoxy)-6-trifluoromethyl-nicotinonitrile;
- 2-(2-methoxy-3-methylaminomethyl-phenoxy)-6-methyl-nicotinonitrile;
- 6-ethyl-2-(2-methoxy-3-methylaminomethyl-phenoxy)-nicotinonitrile;
- 6-methyl-2-(3-methylaminomethyl-phenoxy)-nicotinonitrile;

or a pharmaceutically acceptable salt thereof.

6. A pharmaceutical composition comprising a compound of formula (I) according to any one of claims 1 to 5, or a pharmaceutically acceptable salt thereof, in admixture with a pharmaceutically acceptable adjuvant, diluent or carrier.

7. A method of inhibiting nitric oxide synthase activity in a host, which comprises administering an effective amount of a compound of formula (I), as defined in any one of claims 1 to 5, or a pharmaceutically acceptable salt thereof, to said host.

8. A method of treating inflammation in a person suffering therefrom, wherein the method comprises administering to the person a therapeutically effective amount of a compound of formula (I), as defined in any one of claims 1 to 5, or a pharmaceutically acceptable salt thereof.

9. The method as claimed in claim 8 for treatment of rheumatoid arthritis, osteoarthritis, inflammatory bowel disease or chronic obstructive pulmonary disease.

10. A method of treating pain in a person suffering therefrom, wherein the method comprises administering to the person a therapeutically effective amount of a compound of formula (I), as defined in any one of claims 1 to 5, or a pharmaceutically acceptable salt thereof.

11. The method of treatment as claimed in claim 10 wherein the pain is due to migraine.

12. A process for the preparation of a compound of formula (I), as defined in any one of claims 1 to 5, or a pharmaceutically acceptable salt, enantiomer or racemate thereof, wherein the process comprises:

(a) reaction of a compound of formula (II)

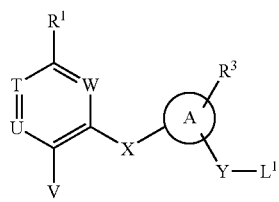

(II)

wherein A, $R^1$, $R^3$, T, U, V, W, X and Y are as defined in claim 1 and $L^1$ is a leaving group,
with a compound of formula (III)

$HNR^4R^5$ (III)

wherein $R^4$ and $R^5$ are as defined in claim 1; or (b) reductive amination of a compound of formula (IV)

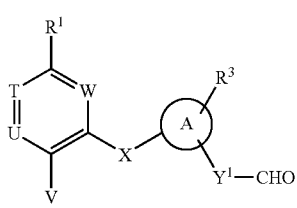

(IV)

wherein A, $R^1$, $R^3$, T, U, V, W and X are as defined in claim 1 and ($Y^1$—$CH_2$) formed by reduction of ($Y^1$—CHO) in formula (IV) represents Y as defined in claim 1, with a compound of formula (III)

$HNR^4R^5$ (III)

wherein $R^4$ and $R^5$ are as defined in claim 1; or (c) reaction of a compound of formula (V)

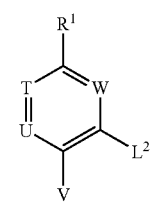

(V)

wherein $R^1$, T, U, V and W are as defined in claim 1 and $L^2$ is a leaving group,
with a compound of formula (VI)

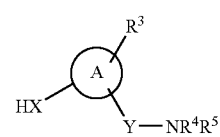

(VI)

wherein A, $R^3$, $R^4$, $R^5$ and Y are as defined in claim 1 and X is O or S; or (d) reaction of a compound of formula (VII)

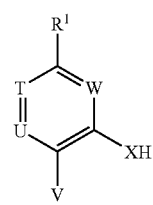

(VII)

wherein $R^1$, T, U, V and W are as defined in claim 1 and X represents O or S,
with a compound of formula (VIII)

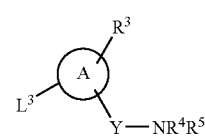

(VIII)

wherein A, $R^3$, $R^4$, $R^5$ and Y are as defined in claim 1 and $L^3$ is a leaving group; or (e) preparing a compound of formula (I) wherein $R^4$ and $R^5$ each represent hydrogen, by reduction of a compound of formula (IX)

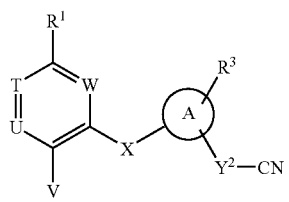
(IX)

wherein A, $R^1$, $R^3$, T, U, V, W and X are as defined in claim 1 and the group ($-Y^2-CH_2-$) formed by reduction of ($Y^2-CN$) in formula (IX) represents Y as defined in formula (I);

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

* * * * *